United States Patent
Minden et al.

(10) Patent No.: US 6,426,190 B1
(45) Date of Patent: *Jul. 30, 2002

(54) DIFFERENCE DETECTION METHODS USING MATCHED MULTIPLE DYES

(75) Inventors: Jonathan Minden; Alan Waggoner, both of Pittsburgh, PA (US); Susan Janet Fowler, Buckinghamshire (GB)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/370,743

(22) Filed: Aug. 9, 1999

Related U.S. Application Data

(63) Continuation-in-part of application No. 08/425,480, filed on Apr. 20, 1995, now Pat. No. 6,127,134.

(51) Int. Cl.$^7$ .......... G01N 33/53; G01N 33/00; C12Q 1/00; C07K 1/00
(52) U.S. Cl. .......... 435/7.2; 435/4; 435/6; 435/7; 435/7.1; 435/7.21; 435/47.2; 436/63; 436/80; 436/86; 436/800; 436/519; 436/546; 436/94; 436/111; 436/131; 530/344; 530/412; 430/581; 430/580; 548/465; 548/469; 544/212
(58) Field of Search .......... 435/4, 6, 7, 7.1, 435/7.2, 7.21, 47.2; 436/63, 80, 86, 800, 519, 546, 94, 111, 131; 530/344, 412; 430/581, 580; 548/465, 469; 544/212

(56) References Cited

U.S. PATENT DOCUMENTS

| | | | |
|---|---|---|---|
| 4,774,339 A | 9/1988 | Haugland et al. | 548/405 |
| 4,855,225 A | 8/1989 | Fung et al. | 435/6 |
| 4,874,492 A | 10/1989 | Mackay | 204/182.8 |
| 5,242,796 A | 9/1993 | Prober et al. | 435/6 |
| 5,248,782 A | 9/1993 | Haugland et al. | 548/110 |
| 5,268,486 A * | 12/1993 | Waggoner et al. | 548/427 |
| 5,274,113 A | 12/1993 | Kang et al. | 548/405 |
| 5,296,599 A | 3/1994 | Cohen et al. | 544/235 |
| 5,307,148 A | 4/1994 | Kambara et al. | 356/344 |
| 5,312,921 A | 5/1994 | Glazer et al. | 546/108 |
| 5,338,854 A | 8/1994 | Kang et al. | 548/110 |

(List continued on next page.)

FOREIGN PATENT DOCUMENTS

| | | | |
|---|---|---|---|
| EP | 0 272 007 A2 | 6/1988 | C09B/11/24 |
| JP | 5-322771 | 12/1993 | G01N/21/76 |
| WO | WO 92/14747 | 9/1992 | C07K/1/14 |
| WO | WO 96/33406 | 10/1996 | G01N/27/447 |

OTHER PUBLICATIONS

Amersham Pharmacia Biotech "BioDirectory '99" catalogue, section entitled "Chromatography Columns and Media", pp. 502–588 (1999).

(List continued on next page.)

Primary Examiner—Long V. Le
Assistant Examiner—Lisa V. Cook
(74) Attorney, Agent, or Firm—Kirkpatrick & Lochart LLP

(57) ABSTRACT

A process and a kit are provided for detecting differences in two or more samples of protein, including proteins bearing post-translational modifications and peptides. Proteins are prepared, for example, from each of a different group of cell samples or body fluid samples to be compared. Each protein extract is labeled with a different one of a luminescent dye from a matched set of dyes. The matched dyes have generally the same ionic and pH characteristics but emit light at different wavelengths to exhibit a different color upon luminescence detection. The labeled protein extracts are mixed together and separated together by electrophoresis or a chromatographic method. The separation is observed to detect proteins unique to one sample or present in a greater ratio in one sample than in the other. Those unique or excess proteins will fluoresce the color of one of the dyes used. Proteins common to each sample migrate together and fluoresce the same.

39 Claims, 11 Drawing Sheets

(3 of 11 Drawing Sheet(s) Filed in Color)

U.S. PATENT DOCUMENTS

| | | | |
|---|---|---|---|
| 5,364,764 A | | 11/1994 | Haugland et al. ............. 435/15 |
| 5,512,486 A | | 4/1996 | Giese et al. ................... 436/63 |
| 5,569,587 A | * | 10/1996 | Waggoner ...................... 435/6 |
| 5,627,027 A | * | 5/1997 | Waggoner ...................... 435/6 |
| 5,654,419 A | | 8/1997 | Mathies et al. ............ 536/25.4 |
| 6,043,025 A | * | 9/2000 | Minden et al. ................. 435/4 |
| 6,127,134 A | * | 10/2000 | Minden et al. .............. 435/7.2 |

OTHER PUBLICATIONS

Opiteck et al., "Comprehensive On–Line LC/LC/MS of Proteins", Anal. Chem., vol. 69, p. 1518–1524 (1997).

Opiteck et al., "Comprehensive Two–Dimensional High–Performance Liquid Chromatography for the Isolation of Overexpressed Proteins and Proteome Mapping", Anal. Biochem., vol. 258, p. 349–361 (1998).

Jensen et al., "Probing Proteomes Using Capillary Isoelectric Focusing–Electrospray Ionization Fourier Transform Ion Cyclotron Resonance Mass Spectrometry", Anal. Chem., vol. 71, p. 2076–2084 (1999).

Wilchek, M and Bayer, E.A., "Labeling Glycoconjugates with Hydrazide Reagents", Methods in Enzymology, vol. 138, pp. 429–442 (1987).

Mujumdar, R.B. et al, "Cyanine Dye Labeling Reagents Containing Isothiocyanate Groups", Cytometry, vol. 10, pp. 11–19 (1989).

Chasman, D.I. et al., "Activation of Yeast Polymerase II Transcription by Herpesvirus VP16 and GAL4 Derivatives In Vitro", Molecular and Cellular Biology, vol. 9, No. 11, pp. 4746–4749 (1989).

Letter to Editor, "HBL–100 Cells Do Not Secrete Casein and Lack Prolactin and Estradiol Receptors", In Vitro Cell Dev. Biol., vol. 26, p. 933–935, Oct. 1990.

Opiteck et al., "Two Dimensional SEC/RPLC Coupled to Mass Spectrometry for the Analysis of Peptides", Anal. Chem., vol. 69, pp. 2283–2291 (1997).

Lasfargues et al., "Isolation of Two Human Tumor Epithelial Cell Lines From Solid Breast Carcinomas", J. Natl. Cancer Inst., vol. 61, No. 4, p. 967–973, Oct. 1978.

Bhargava et al., "Phosphorylation of parathyroid secretory protein", Proc. Natl. Acad. Sci., vol. 80, pp. 878–881, Feb. 1983.

Wayne F. Patton, "A thousand points of light: The application of fluorescence detection technologies to two–dimensional gel electrophoresis and proteomics", Electrophoresis, vol. 21, pp. 1123–1144 (2000).

L.M. Smith et al., Fluorescence Detection in Automated DNA Sequence Analysis, Nature vol. 321, pp. 674–678, Jun. 12, 1986.

Amersham Life Science Products Catalogue (1991) p. 61, Illinois USA "Rainbow protein molecular weight markers".

Juan F. Santaren et al., Identification of Drosophila Wing Imaginal Disc Proteins by Two–Dimensional Gel Analysis and Microsequencing, Experimental Cell Research 206, 220–226, 1993.

James I. Garrels, Two–Dimensional Gel Electrophoresis and Computer Analysis of Proteins Synthesized by Clonal Cell Lines, The Journal of Biological Chemistry, vol. 254, No. 16, Issue of Aug. 25, pp. 7961–7973, 1979.

Peter Jackson et al., Rapid imaging, using a cooled charged–coupled–device, of fluorescent two–dimensional polyacrylamide gels produced by labelling proteins in the first–dimensional isoelectric focusing gel with the fluorophore 2–methoxy–2, 4–diphenyl–3 (2H) furanone, Electrophoresis, vol. 9, pp. 330–339, 1988.

Patrick H. O'Farrell, High Resolution Two–Dimensional Electrophoresis of Proteins, The Journal of Biological Chemistry, vol. 250, No. 10, Issue of May 25, pp. 4007–4021, 1975.

Valerie E. Urwin et al., A Multiple High–Resolution Mini Two–Dimensional Polyacrylamide Gel Electrophoresis System: Imaging Two–Dimensional Gels using a Cooled Charge–Coupled Device after Staining with Silver or Labeling with Fluorophore, Analyical Biochemistry, vol. 195, pp. 30–37, 1991.

Richard P. Haughland, Handbook of Fluorescent Probes and Research Chemicals, $5^{th}$ Edition, pp. 203–214, 1992–1994.

R.F. Steiner, Excited States of Biopolymers, pp. 29–58./ Richard P. Haughland Pienum Press, N.Y. 1983.

U.K. Laemmli, Cleavage of Structural Proteins during the Assembly of the Head of Bacteriophage T4, Nature vol. 227, pp. 680–685, Aug. 15, 1970.

Biological Detection Systems, Inc., "FluoroLink–Ab™ Cy5™ Labelling Kit" 1995 Cat. No. A35000.

Biological Detection Systems, Inc., "Fluorolink Labeling Reagents" 1999.

Molecular Probes, Inc., "Conjugation with Amine–Reactive Probes", Product Information Sheet 1999.

* cited by examiner

Labeling of model glycoproteins – analysis by SDS-PAGE

Cy 2 lysine labeling of protein

Cy 3 hydrazide labeling

← Transferrin → (~76 kDa)

← Trypsin → inhibitor (~ 20 kDa)

(a)　　　(b)

Differential SDS-PAGE analysis of simple protein mixes.

Cy3 hydrazide labeling

Cy5 hydrazide labeling

← Transferrin →
(~76kDa)

← Carbonic anhydrase →
(~30 kDa)

(a)

(b)

Differential 2DE analysis of mammalian cell extracts

Cy3 hydrazide labeling of HBL100 cell extract

Cy5 hydrazide labeling of BT474 cell extract (a)          (b)

Arrows indicate some of the qualitative and quantitative differences between the two cell extracts.

Ion exchange chromatography of Cy3 and Cy5 labeled proteins

Ion exchange chromatography of a mixture of Cy5 labeled proteins

Reverse phase chromatography of a mixture of Cy5 labeled proteins

Size exclusion chromatography of a mixture of Cy3 labeled proteins

Differential analysis of mixtures of Cy3 and Cy5 labeled proteins by size exclusion chromatography Differential analysis of mixtures of Cy3 and Cy5 labeled proteins by ion exchange chromatography

DIFFERENCE DETECTION METHODS USING MATCHED MULTIPLE DYES

CROSS REFERENCE TO RELATED APPLICATIONS

This is a continuation-in-part of U.S. application Ser. No. 08/425,480, filed Apr. 20, 1995, now U.S. Pat. No. 6,127,134.

BACKGROUND OF THE INVENTION

The present invention relates to a process for detecting differences in protein compositions, including proteins bearing post-translational modifications, and more particularly, to a process utilizing a matched pair of labeling reagents for detecting such differences.

Researchers studying various aspects of cell biology use a variety of tools to detect and monitor differences in cell structure, function and development. An essential part of studying cells is studying the differences and similarities in the protein composition between the different cell types, stages of development and condition. Determining differences in the protein content between normal and cancerous cells or wild type and mutant cells, for example, can be a valuable source of information and a valuable diagnostic tool.

Mixtures of proteins can be separated into individual components by various means, including electrophoresis and chromatography. Separation according to differences in mass can be achieved by electrophoresing in a polyacrylamide gel under denaturing conditions. One dimensional and two dimensional gel electrophoresis have become standard tools for studying proteins. One dimensional SDS (sodium dodecyl sulfate) electrophoresis through a cylindrical or slab gel reveals only the major proteins present in a sample tested. Two dimensional polyacrylamide gel electrophoresis (2D PAGE), which separates proteins by isoelectric focusing, i.e., by charge in one dimension and by size in the second dimension, is the more sensitive method of separation and will provide resolution of most of the proteins in a sample.

The proteins migrate in one- or two-dimensional gels as bands or spots, respectively. The separated proteins are visualized by a variety of methods; by staining with a protein specific dye, by protein mediated silver precipitation, autoradiographic detection of radioactively labeled protein, and by covalent attachment of fluorescent compounds. The latter method has been heretofore only able to be performed after the isoelectric focusing step of 2D PAGE. Immediately following the electrophoresis, the resulting gel patterns may be visualized by eye, photographically or by electronic image capture, for example, by using a cooled charge-coupled device (CCD).

To compare samples of proteins from different sources, such as different cells or different stages of cell development by conventional methods, each different sample is presently run on separate lanes of a one dimensional gel or separate two dimensional gels. Comparison is by visual examination or electronic imaging, for example, by computer-aided image analysis of digitized one or two dimensional gels.

Two dimensional electrophoresis is frequently used by researchers. O'Farrell, P. H., "High resolution two-dimensional electrophoresis of proteins", Journal of Biological Chemistry, 250:4007–4021 (1975), separated proteins according to their respective isoelectric points in the first dimension by the now well known technique of isoelectric focusing and by molecular weight in the second dimension by discontinuous SDS electrophoresis. Garrels, J. I., "Two-dimensional Gel Electrophoresis and Computer Analysis of Proteins Synthesized By Clonal Cell Lines", Journal of Biological Chemistry, Vol. 254, No. 16, 7961–7977 (1979), used a two dimensional gel electrophoresis system to study the pattern of protein synthesis in nerve cells and glial cells. Garrels conducted a comparative analysis of data from multiple samples to correlate the presence of particular proteins with specific functions. Computerized scanning equipment was used to scan a section of the gel fluorogram, detect the spots and integrate their densities. The information was stored and plotted according to intensity in each of several different scans.

Urwin, V. E. and Jackson, P., "A multiple High-resolution Mini Two-dimensional Polyacrylamide Gel Electrophoresis System: Imaging Two-dimensional Gels Using A Cooled Charge-Coupled Device After Staining With Silver Or Labeling With Fluorophore", Analytical Biochemistry 195:30–37 (1991) describes a technique wherein several isoelectric focusing (IEF) gels were used to separate proteins by charge, then loaded onto a gradient slab gel such that the IEF gels were positioned end to end along the top of the slab gel. The gels were then electrophoresed. The resulting protein spots were visualized either by staining the second dimensional slab gel with silver or by fluorescent labeling following the isoelectric focusing step. Labeling must take place after the first electrophoresis, i.e., the isoelectric focusing because the presence of the fluorescein label on the protein changes the isoelectric point of the protein when subjected to electrophoresis. In addition, the label attaches to a sulfur on the protein forming an unstable bond which would tend to break during isoelectric focusing if the label is attached prior to the electrophoresis step. An article by Santaren, J. et al., "Identification of Drosophila Wing Imaginal Disc Proteins by Two-Dimensional Gel Analysis and Microsequencing", Experimental Cell Research 206: 220–226 (1993), describes the use of high resolution two dimensional gel electrophoresis to identify proteins in *Drosophila melanogaster*. The dry gel was exposed to X-ray film for five days. The developed X-ray film is analyzed by a computer to determine the differences in the samples.

Two dimensional gel electrophoresis has been a powerful tool for resolving complex mixtures of proteins. The differences between the proteins, however, can be subtle. Imperfections in the gel can interfere with accurate observations. In order to minimize the imperfections, the gels provided in commercially available electrophoresis systems are prepared with exacting precision. Even with-meticulous controls, no two gels are identical. The gels may differ one from the other in pH gradients or uniformity. In addition, the electrophoresis conditions from one run to the next may be different. Computer software has been developed for automated alignment of different gels. However, all of the software packages are based on linear expansion or contraction of one or both of the dimensions on two dimensional gels. The software cannot adjust for local distortions in the gels.

Protein samples may also be separated by alternative electrophoretic or chromatography techniques. Such techniques are capable of high-resolution separation of proteins or peptides particularly in orthogonal combinations. However, current chromatographic systems tend to have lower resolving power than electrophoretic systems, ie the number of proteins or peptides capable of being separated is smaller. Typical elution traces can be found in manufacturers' catalogues, e.g., Amersham Pharmacia Biotech "Bio- Directory '99" catalogue under "Chromatography columns and media" starting at page 502. Nevertheless, chromatographic systems do have certain advantages over electrophoresis for some applications. For example, they are often easier to automate and it is usually easier to obtain samples of the proteins following separation.

For these reasons, separation by chromatographic systems for proteome profiling for example, is of interest. For example, Opiteck and colleagues have published examples of two-dimensional chromatographic systems where fractions eluted from a chromatographic separation system are applied to a second chromatographic system. (See specifically, Opiteck, Lewis and Jorgenson, Anal. Chem, vol. 69, 1518, (1997) which describes the use of a cation exchange system in combination with a reverse phase chromatographic system, and Opiteck et al., Anal Biochem., vol. 258, 349, (1998), which describes the use of size exclusion chromatography in combination with reverse phase chromatography.) The particularly low resolving power of size exclusion chromatography is alleviated in the latter paper by using 8 size exclusion columns in series prior to further fractionation of the eluent by reverse phase chromatography. A theoretical resolving power of 800 proteins was estimated for this system. The limited resolving power of certain chromatographic and electrophoretic systems can also be overcome at the analysis stage. Mass spectrometry is becoming widely used for protein identification following chromatographic or electrophoretic separation and can itself be used as a separation method based on mass. For example, Jensen et al., Anal. Chem. Vol. 71, 2076, (1999) describes the use of capillary isoelectric focusing as a separation method and then uses electrospray ionisation Fourier transform ion cyclotron resonance mass spectrometry to further separate proteins in the eluent from the isoelectric focusing system, as well as provide a means of identification.

The object of the present invention is to eliminate the problems associated with gel distortions or column variability and to provide a simple, relatively fast and reliable method of comparing and contrasting the protein content of different samples.

BRIEF SUMMARY OF THE INVENTION

The foregoing objects have been achieved by the process of the present invention wherein differences, if any, between multiple samples of proteins, for example, those extracted from different cells or obtained from other sources, are detected by labeling each sample of such proteins with a different one of a set of matched luminescent dyes. Proteins, as used herein, includes proteins bearing post translational modifications and portions thereof, including peptides. The matched dyes have generally the same ionic and pH characteristics but absorb and/or fluoresce light at different wavelengths, producing a different color fluorescence. In addition, the dyes should be similar in size. After an incubation period sufficient to permit the formation of covalent bonds between the dye and one or more attachment sites on the proteins, the labeled samples are then mixed together and the proteins separated in a single separation process. Separation may be by electrophoresis or by chromatographic methods. When separation is by electrophoresis on a single gel, the proteins common to each sample co-migrate to the same position. Similarly, when separation is by chromatographic means in a column, for example, the proteins common to each sample migrate to the same position. Proteins which are different will migrate alone to different locations on the gel or at different times from the column and will fluoresce different colors, thereby identifying which initial sample has one or more proteins which differ from the other initial sample or samples.

The invention also includes a kit for performing the method of the present invention. The kit includes the matched set of dyes, and may also include materials for separating the proteins. Quench materials for stopping the reaction between the protein and the dye when necessary, may optionally be provided. Those materials may comprise, for example, electrophoresis gels or chromatography columns.

DESCRIPTION OF THE DRAWINGS

The file of this patent contains at least one drawing executed in color. Copies of this patent with color drawings are provided to the Patent and Trademark Office with payment of the necessary fee.

DETAILED DESCRIPTION OF THE PREFERRED EMBODIMENTS

The process of the present invention employs a matched set of dyes wherein each dye in the set is generally equal to the other dyes in ionic and pH characteristics, and chemical reactivity for covalent attachment to proteins, yet fluoresces at a different wavelength, thereby exhibiting a different color luminescence when viewed. The dyes are preferably roughly equal in molecular weight, but need not be. Each one of the dyes within the matched set of dyes is used to label proteins in a different one of a set of different samples of proteins so that each sample is labeled with a different dye within the set of dyes. After labeling, the proteins are mixed and separated in the same medium by any suitable known separation technique, such as electrophoresis or chromatography. Electrophoresis techniques include one or two dimensional electrophoresis, capillary zone electrophoresis, capillary gel electrophoresis, isoelectric focussing, isotacophoresis, and micellar electrokinetic chromatography. Chromatographic techniques include affinity chromatography, size exclusion chromatography, reverse phase chromatography, hydrophobic interaction chromatography and ion exchange chromatography.

Figure 1:
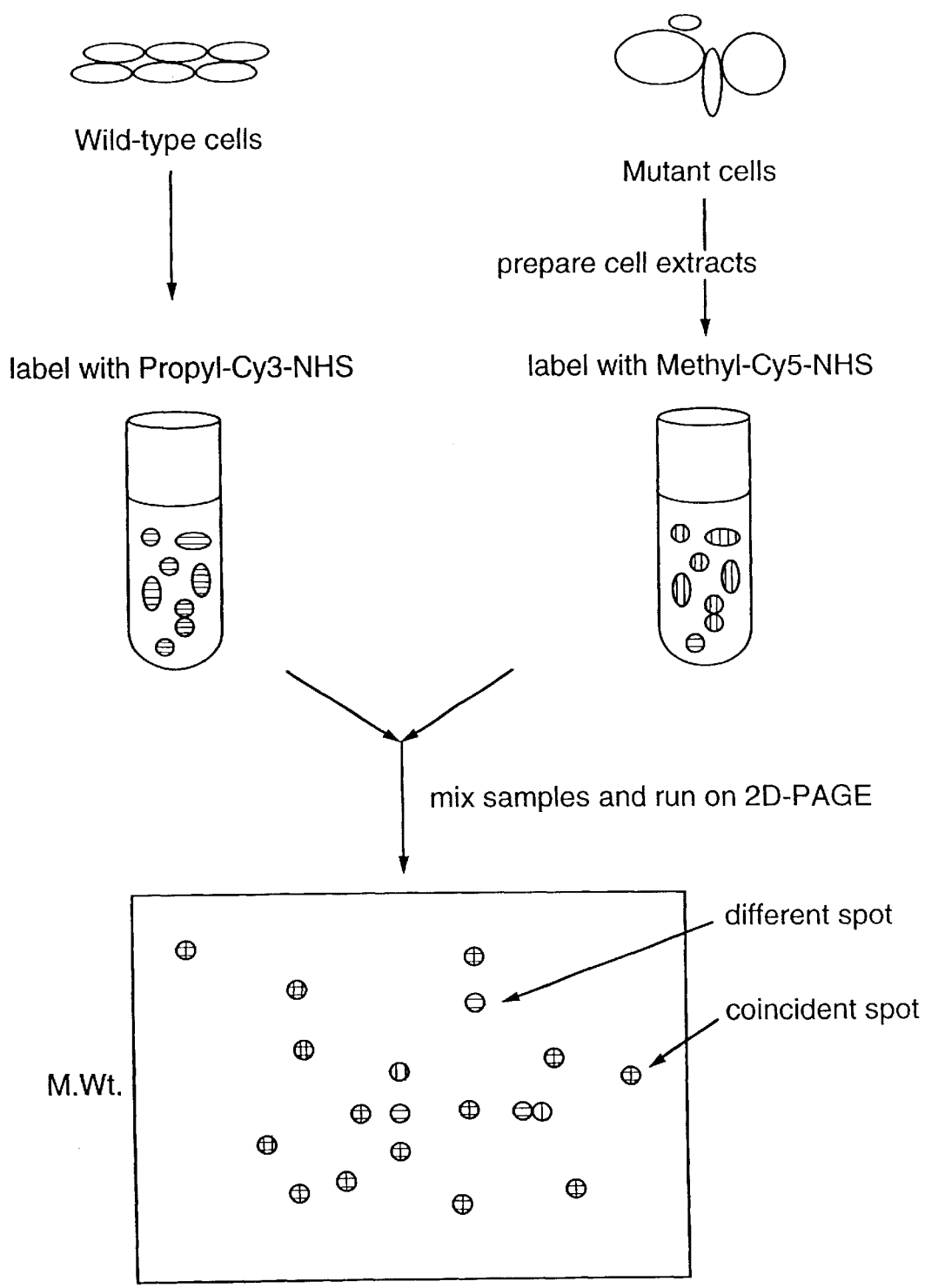
FIG. 1 is a schematic diagram of the process of the present invention.

With reference to the schematic diagram of FIG. 1, a first extract of proteins is prepared by known techniques from a first group of cells, then labeled with the first dye of a matched pair of dyes. A second extract of proteins is prepared by known techniques from a second group of cells then labeled with the second dye of the matched pair of dyes. To label the protein, the reactive form of the dye and the protein are incubated for a period of time sufficient to allow for the formation of a covalent bond between the reactive form of the dye and potential attachment or binding sites on the proteins. The period of time is generally from 15 to 30 minutes, depending on the temperature. The temperature range is generally from about 0° C. to 25° C. The reaction between the dye and the proteins may be quenched after a sufficient percentage of available binding sites on the protein molecule are covalently bound to the dye. Any suitable known quenching material may be used. Other methods for removal of excess dye, such as gel filtration, may also be used. In situations where the labelling reaction is allowed to go to completion, for example when all the reactive dye has been used, quenching or removal of excess dye may not be required.

The first and second group of cells can be any two sets of cells the protein content of which one wishes to compare or contrast. For example, the first group of cells can be the wild-type, or normal, cells, and the second group of cells can be mutant cells from the same species. Alternatively, the first group of cells can be normal cells and the second group can be cancerous cells from the same individual. Cells from the same individual at different stages of development or different phases of the cell cycle can be used also. The cells from a developing embryo, from the ventral furrow of *Drosophila melanogaster*, for example, can be harvested as the first group of cells and cells that develop adjacent to the ventral furrow cells can be harvested as the second group of cells. The differences in protein composition between cells of the same type from different species can also be the subject of study by the process of the present invention. In addition, the process of the present invention can be used to monitor how cells respond to a variety of stimuli or drugs. All of the events that might alter cell behavior as expressed through protein changes can be detected without the need and expense of high precision 2D PAGE systems. Those skilled in the art will recognize that the proteins for comparison may also be derived from biological fluids, such as serum, urine, or spinal fluid.

The labeled samples are mixed and, as illustrated in FIG. 1, applied in measured aliquots to one gel, then preferably subjected to 2D PAGE. One dimensional SDS electrophoresis can be used instead of 2D PAGE. The procedures for running one dimensional and two dimensional electrophoresis are well known to those skilled in the art.

Proteins that the two cell groups have in common form coincident spots. The ratio of the fluorescent intensity between identical proteins from either group will be constant for the vast majority of proteins. Proteins that the two groups do not have in common will migrate independently. Thus, a protein that is unique or of different relative concentration to one group will have a different ratio of fluorescence intensity from the majority of protein spots, and will produce a color specific for one or the other of the protein extracts, depending on the label used. For example, the proteins that are in the first sample may be labeled red, while the second group is labeled blue. Under conditions where exactly equal amounts of protein from each group is mixed together and run on the same gel the ratio of fluorescence intensity will be one for the majority of proteins. Those proteins that are distinct to one or the other group will have a fluorescence intensity ratio less than or greater than one, depending on the order or ratioing.

The gel can be analyzed by a two wavelength fluorescence scanner, by a fluorescent microscope or by any known means for detecting fluorescence. Gel analysis can be completely automated by means of computer aided identification of protein differences. Using an electronic detection system such as a laser scanning system with a photo multiplier tube or a charged-coupled device (CCD) camera and a white light source, two electronic images are made of the wet gel using different known filter sets to accommodate the different spectral characteristics of the labels. One image views fluorescence of the first dye using a first filter appropriate to filter out all light except that emitted at the wavelength of the first dye and the other image, views fluorescence of the second dye using a second filter, appropriate to filter out all light except that emitted at the wavelength of the second dye. Exposure is about 5 to 500 seconds. The differences in the samples can be identified, either during electrophoresis or in less than ½ hour following electrophoresis. Several software packages are commercially available which will either subtract the first image from the second to identify spots that are different, or, alternatively, the images may be divided to leave only the spots not common to both images. In subtracting the images, like spots will cancel each other, leaving only those that are different. In ratio analysis, like spots will provide a value of one. Differences will result in values greater, than one less than one.

In conventional analysis, a control is run with known proteins for the cell type being studied. The known spots on the sample gel have to be identified and marked, compared to the control and the second gel to determine differences between the two gels. In the present invention, there is only one gel so no marking is necessary. In addition, the software used on conventional processes for alignment of different gels prior to comparing and contrasting protein differences does not correct for local distortions and inconsistencies between two or more gels. The process of the present invention eliminates the need for such correction because the labeled proteins for all samples to be tested are mixed and separated together. Any distortions in an electrophoresis gel, for example, are experienced equally by each sample.

Selection and synthesis of the matched set of dyes is important. In the process of the present invention, the fluorescent dyes are covalently coupled to proteins, preferably via lysine residues of the proteins, but coupling may also be to sulfhydryl or carboxylic acid groups in the proteins. For modified proteins, the dyes may be coupled to the modifying groups; for example the dyes may be coupled to the sugar residue of glycoproteins following oxidation thereof to the aldehyde. Regulation of the pH of proteins to force attachment of labels at one amino acid residue to the exclusion of other amino acids is a well known technique, as set forth in R. Baker, Organic Chemistry of Biological Components, (Prentice Hall, pub. 1971). For analysis of proteins, a plurality of attachment sites are labeled. The optimum percentage of attachment sites labeled will depend on the dyes and target functional groups chosen. When the preferred dyes specifically discussed hereinbelow are used to label lysines; preferably no more than 2% of the attachment sites and more preferably, slightly less than 1%, are labeled, to avoid rendering the protein insoluble. Thus, where a typical protein is composed of about 7% lysines, there will be less than one modified amino acid per one thousand. A typical protein is composed of about 450 amino acids. An alternative strategy is to label all the functional groups of a particular type which is less prevalent in the protein, for example sulfhydryl groups in cysteines. When lysine is the attachment site, the covalent linkage destroys the positive charge of the primary amine of the lysine. Because isoelectric focusing depends on charge, it is important to compensate for the charge loss. A basic residue should remain basic. Changing the pKa of one residue per protein by as much as 3 can be tolerated, provided the basicity or acidity of the modified residue, as the case may be, is not altered. Dyes like rhodamine and fluorescein are not suitable because of the difference in charge.

Those skilled in the art will recognize that the labeling approaches described could equally well be applied to peptide molecules derived from cells or present in biological fluids such as plasma, serum, urine, ascites or spinal fluid. Furthermore, in preparing a protein sample for labeling it may, in certain circumstances, be beneficial to first perform an enzyme digestion with trypsin or other protease enzymes to generate peptides prior to labeling and separation.

As an alternative, it is possible to target specific groups of proteins, such as proteins bearing post-translational modifications, in order to compare differences in the post-translational modifications and other differences occurring in proteins between two or more samples.

An example of such proteins is the glycoproteins. In recent years, the functional significance of carbohydrate on proteins has been increasingly realized. Carbohydrates are now known to be implicated in many cellular and disease processes. It is possible to label the terminal carbohydrate groups of glycoproteins by first oxidizing the terminal sugars to aldehydes, followed by reaction with a hapten or a fluor bearing a reactive group such as a hydrazide, as described by Wilchek, M and Bayer, E. A., "Methods in Enzymology" vol. 138, 429–442 (1987).

More specifically this would involve: Preparing an extract of two or more protein samples, incubating each of said protein samples in the presence of periodate for a short period to oxidise vicinal diols on the terminal sugars to aldehyde groups. Excess periodate would then be destroyed by adding bisulphite, before labeling with a suitable fluorescent dye from a matched set. Alternatively, it is possible to specifically label sialic acid residues by oxidation of their exocyclic carbons using a lower concentration of periodate, typically 1 mM and using a temperature of 0° C. It is also possible to treat the protein sample with galactose oxidase to generate an aldehyde group on terminal galactose residues to form a C-6 aldehyde derivative, which can then be reacted with a suitable fluor. The reaction of the dye and the carbohydrate may be quenched by the addition of suitable material before mixing samples together and subjecting to a suitable separation method.

Fluorescent dyes that can be used for glycoprotein labeling include those dyes having hydrazine derivatives such as hydrazides, semicarbazides and carbohydrazides or amine derivatives as reactive groups. In order to maintain the overall charge on the glycoprotein, suitable dyes are those that bear an overall neutral charge. An overall neutral charge can be obtained by the addition of suitably charged linkers to the dye molecule to produce the desired overall charge. Suitable dyes would include neutral cyanine derivatives, BODIPY® fluorescent dye derivatives or other fluorescent derivatives available as matched dye sets as described herein and possessing an overall neutral charge.

The method of the present invention is also applicable to phosphoproteins which may be specifically labeled with fluors. Phosphoproteins perform important biological roles, including cell signaling, and are involved in a number of regulatory mechanisms. The phosphate groups on proteins may be specifically labeled as, for example, by the procedure described by Giese and Wang, U.S. Pat. No. 5,512,486, incorporated herein by reference, using fluorescent or hapten imidazole derivatives. The labeling reagents bearing the imidazole groups are added to the protein samples in the presence of a suitable carbodiimide to effect labeling.

More specifically the method involves preparing an extract of two or more protein samples, incubating each of said protein samples with a suitable water-soluble carbodiimide, plus a fluorescent imidazole derivative from a matched dye set. Although the carbodiimide will activate side chain carboxyls as well as phosphates, the bond with carboxyl groups is unstable when the pH is raised to around 8. Excess reactive material can be removed by the addition of a suitable known quenching material. The samples are then mixed and separated by a known separation procedure.

In order to maintain the overall charge on the phosphoprotein, suitable fluorescent imidazole derivatives would bear an overall negative charge. This overall negative charge could be obtained by the addition of a suitably charged linker to the dye molecule. Examples of dyes that can be used include, cyanine dyes bearing an overall negative charge, squarate dye derivatives bearing an overall negative charge or other fluorescent derivatives bearing an overall negative charge and available as matched dye sets. Preferred carbodiimide molecules are water soluble molecules such as (1-ethyl-3-(3-dimethylaminopropyl)-carbodiimide hydrochloride) (EDC) and 1-ethyl-3-(4-azonia-4,4-dimethylpentyl)carbodiimide iodide) (EAC).

The first group of dyes evaluated were the fluorescent cyanine dyes described in Mujumdar, R. B. et al., "Cyanine dye labeling reagents containing isothiocyanate groups", Cytometry 10:11–19 (1989) and Waggoner et al., U.S. Pat. No. 5,268,486 entitled "Method for labeling and detecting materials employing arylsulfonate cyanine dyes" issued in 1993 and incorporated herein by reference. The cyanine dyes have the following general structure.

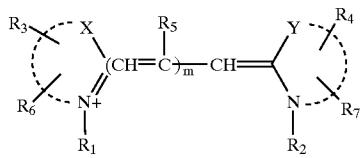

where X and Y can be O, S or $(CH_3)_2$—C, m is an integer from 1 to 3 and at least one of $R_1$, $R_2$, $R_3$, $R_4$, $R_5$, $R_6$ or $R_7$ is a reactive group which reacts with amino, hydroxy or sulfhydryl nucleophiles. The dotted lines represent the carbon atoms necessary for the formation of one ring to three fused rings having 5 to 6 atoms in each ring. $R_3$, $R_4$, $R_6$ and $R_7$ are attached to the rings. The reactive moiety can be any known reactive group. Reactive groups that may be attached directly or indirectly to the chromophore to form $R_1$, $R_2$, $R_3$, $R_4$, $R_5$, $R_6$ or $R_7$ groups may include reactive moieties such as groups containing isothiocyanate, isocyanate, monochlorotriazine,, dichlorotriazine, mono- or di-halogen substituted pyridine, mono- or di-halogen substituted diazine, maleimide, phosphoramidite, aziridine, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal, ketone, amino and aldehyde.

Because of their intrinsic positive charge, the cyanine dyes described in the Waggoner et al. patent are the fluorophors of choice when a positive charge is desired for labeling primary amines. The cyanines attach to the protein via the activated ester of hexanoic acid. While the coupling destroys the charge of the lysine side chain, the intrinsic charge in the dye compensates. It in effect moves the charge away from the protein molecule but maintains the same overall charge within the sample to be electrophoresed. In the cyanine dye molecule, two functionalized indole rings are connected via a polyene linker. The spectral characteristics of cyanine dyes can be easily modulated by simply changing the length of the linker between the indole rings of the dye. A longer or shorter linker length will result in fluorescence at different wavelengths and thus, different colors. However, changing the length of the linker changes the molecular mass of the dye. Since electrophoresis depends also on the mass of the proteins, the effect of the dye on a protein's mass can also be of concern. Because the proteins are labeled before electrophoresing, the mass of the dye attached to the protein must not significantly alter the relative differences in the molecular weights of the various proteins in the extracts. Molecular weight is not critical, however, because only a relatively small number of sites on the protein are labeled. As indicated above, preferably less than 1%, up to about 2% of the possible attachment sites on the proteins are labeled. If more are labeled, maintaining generally equal molecular weights for the dyes within the set of matched dyes becomes a greater concern.

The difference in molecular weight caused by changing the linker length in the fluorescent cyanine dyes can be compensated for by modulating the size of an aliphatic chain $R_1$ or $R_2$, attached to one of the dye's indole rings. One of $R_1$ or $R_2$ must be a reactive group. These design constraints led to the modification of the cyanines and the development of a dye of the general formula

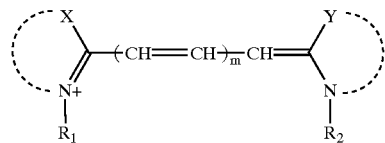

wherein X and Y equal S, O, or $CH_3$—C—$CH_3$, m is an integer from 1 to 3 and either $R_1$ or $R_2$ is a reactive group capable of covalently binding to the protein, such as the reactive groups described above for the unmodified cyanine dyes. The dotted lines represent 1, 2 or 3 fused rings having 5 or 6 carbon atoms in each ring. Each side should balance the other side.

An example of a matched pair of dyes developed according to the general formula follows:

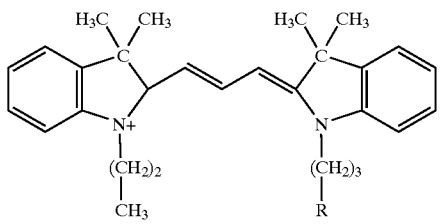

(Propyl Cy-3-NHS) which fluoresces red and,

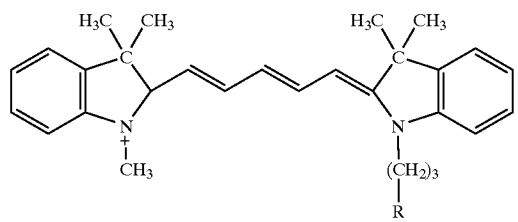

(Methyl Cy-5-NHS) which fluoresces far red in the spectrum wherein R is a reactive group. As stated above, O or S or a combination thereof can be placed in the X and Y positions in place of $(CH_3)_2C$—.

The cyanine dyes are one choice for the matched set of dyes of the present invention. Other dye compounds may be used in place of the cyanines, such as dipyrromethene boron difluoride dyes, the derivatized The cyanine dyes are one choice for the matched set of dyes of the present invention. Other dye compounds may be used in place of the cyanines, such as dipyrromethene boron difluoride dyes, the derivatized 4,4-difluoro-4-bora-3a,4a,-diaza-S-indacene dyes, described in U.S. Pat. No. 4,774,339 to Haugland et al. and incorporated herein by reference, which are sold by Molecular Probes, Inc. under the trademark BODIPY®. The BODIPY® fluorescent dyes, which have no net charge, are covalently linked to lysine side chains using an activated n-hydroxysuccinimidyl ester which forms an amide bond. The result is the loss of the lysine positive charge. Therefore, a positively charged linker group is used in the matched dyes of the invention to replace the lost primary amine with the linker's tertiary amine. The procedures for making BODIPY® fluorescent dyes are described in U.S. Pat. No. 4,774,339. Addition, of the positively charged linker is by techniques well known to those skilled in the art. A linker can be designed with three functional groups; (1) to react with the BODIPY®-NHS ester, (2) to carry the desired charge, and (3) to be activated so that the BODIPY®-linker construct will react with specific amino acid residues of the proteins in the extract.

The major considerations for the matched set of dyes are the maintenance of charge and distinct and different spectral characteristics. Any neutral dyes with a positive linker or any positively charged dyes, preferably each having a +1 charge, that otherwise satisfy the requirements described herein can serve as the dyes in the matched set of dyes of the present invention. Roughly equal molecular weight in the samples of labeled protein is desirable, but as explained above, not critical. The intrinsic positive charge of cyanine dyes is advantageously used in the preferred embodiment to replace the positive charge of lysine. The $pK_a$ of cyanines and lysine are rather different; however, conditions were selected for dye:protein ratio to be less than one. This low level of labeling ensures that there will be negligible changes in the protein's migration on two-dimensional electrophoresis gels. Dyes may be used which match the $pK_a$ of lysine more closely. Alternately, dyes that modify other amino acid residues may be used, provided the amino acid's ionic characteristics are preserved by the modification. Instead of a lysine, the attachment site on the protein may be a sulfhydryl or carboxylic group. When a sulfhydryl group is the attachment site on the protein, the corresponding attachment site on the dye is an iodoalkyl or maleimide group. When a carboxylic acid group is the attachment site on the protein, the corresponding attachment site on the dye is a chloroketone or a carbodiimide.

It is anticipated that the method of the present invention also can be used to detect the presence of different nucleic acids in different samples. The charge of nucleic acids is very negative. The addition of the dye does not therefore alter the overall charge in nucleic acids so the choice of the matched set of dyes does not have to compensate for charge loss when nucleic acid analysis is contemplated. To facilitate attachment of the dye, nucleic acids can be modified to have a free amino acid coming from the nucleic acid nucleus by techniques known to those skilled in the art. A lysine would be suitable in this instance also.

EXAMPLE 1
Synthesis of the Dyes (Methyl Cy-5 and Propyl Cy-3)

1. Synthesis of Indole Derivatives (Common to Both Dyes)

4.8 g (30 mmoles) of 2,3,3-trimethyl-(3H)-indole and 35 mmoles of the desired bromoalkyl reagent (6-bromohexanoic acid or 1-bromopropane) in 40 ml of 1,2-dichlorobenzene were heated to 110° C. under nitrogen gas and stirred overnight with refluxing. The product (acid indole, methyl indole, or propyl indole) precipitated as an orangish gum. The supernatant was decanted and the gum was washed several times with ethyl ether. This intermediate was used as is.

2. Cy-3 Intermediate 1.5 g (7.5 mmoles) of propyl indole was added to 1.6 g (7.6 mmoles) of N-N' diphenyl formamidine in 20 ml glacial acetic acid and was refluxed for 4 hrs. The solvent was removed under vacuum leaving a deep orange syrup. This intermediate was used as is.

2a. Cy-5 Intermediate

The synthesis of the Cy-5 intermediate is the same as the synthesis of the Cy-3 intermediate in step 2 of the dye synthesis except that 2-methylene-1,3,3-trimethylindoline was used instead of propyl indole and the linker was malonaldehyde dianil. The gummy, bluish intermediate was washed twice with ethyl ether.

3. Cy-3

2.5 ml of triethylamine and 1.8 ml of anhydrous $Ac_2O$ were added to the intermediate from step 2., and the mixture was boiled for 5 minutes. 1.70 g (5.0 mmoles) of acid indole was added and the mixture was refluxed for two hours. The solvent was removed under vacuum and the products were dissolved in 10 ml of EtOH.

3a. Cy-5

The preparation of Cy-5 is the same as that of Cy-3 except that the intermediate from step 2a. was used instead of the intermediate from step 2.

4. Purification of the Products from Steps 3. and 3a.

Methyl Cy-5 and propyl Cy-3 were separated from contaminating side products by running flash chromatography with a silica gel solid phase and 40% MeOH in dichloromethane as the mobile phase.

5. Activation of Carboxyl Groups

The carboxylic acid moiety of each dye was converted into an N-hydroxysuccinimidyl ester by dissolving a quantity of purified material in 5 ml of dry dimethylformamidine (DMF). 1.5 equivalents of N-N' disuccinimidyl carbonate (DSC) was added with 0.1 ml dry pyridine/100 mg dye. The reaction was refluxed at 60° C. for 90 minutes under nitrogen.

EXAMPLE 2
Protein Labeling

1. Bacterial Culture

Initial experiments were performed on *E. coli* that expressed the chimeric GAL4VP16 protein under the control of the lac promoter as described in Chasman, D. I. et al., "Activation of yeast polymerase II transcription by Herpesvirus VP16 and GAL4 derivatives in vitro", Molecular Cell Biology 9:4746–4749 (1989). Two cultures of bacteria were grown to an OD600 of 0.7 at 37° C. in 125 ml of standard LB medium containing 50 µg/ml ampicillin. Isophenylthiogalactopyranoside (IPTG), a non-hydrolyzable analog of lactose, was added to one culture at a final concentration of 1 mM. Both cultures were incubated for an additional 2.5 hours.

2. Protein Isolation for Two-dimensional Gel Electrophoresis

Isolation of protein was as follows. The bacteria was isolated by centrifugation. Each bacterial pellet was washed with sonication buffer containing 5 mM Hepes KOH pH 8.4, 5 mM $Mg(OA_c)2$. The pellet was resuspended in sonication buffer containing 50 µg/ml RNase to a final volume of 100 µl. This was then sonicated in ice until the solution was clear, usually several minutes. DNase was added to 50 µg/ml and the sample was incubated for 30 min at 0° C. Solid urea and CHAPS were added to a final concentration of 8 M and 5% respectively. The sample was taken off the ice and 1 volume of lysis buffer added. The sample was either labeled immediately or stored at –80° C.

3. Protein Labeling

Propyl Cy-3-NHS was added to the first sample and Methyl Cy-5-NHS was added to the second sample of cell extract at a concentration of 2 mmole of dye/50 µg of protein. The dye stock solution was typically 2 mM in dimethyl formamide. The reaction was incubated at 0° C. for 30 minutes. Incubation times may vary from about 15 to about 30 minutes, depending on the temperature and the type of cells being studied. Incubation can be for 15 minutes when the temperature is about 25° C. The temperature should not be above that which will cause the proteins to be degraded. The labeled sample was immediately subjected to isoelectric focusing or stored at –80° C.

4. Protein Isolation and Labeling for SDS-gel Electrophoresis

Bacteria were grown and isolated by sonication as in step 2, of the protein labeling procedure, except RNase or DNase was not added. The cell extract was directly labeled as in step 3 of the protein labeling procedure. SDS, glycerol, Tris HCl pH 6.8, and bromophenol blue were added to bring the final concentrations to 1%, 10%, 64 mM, and 5 µg/ml, respectively. The sample was then placed in a boiling water bath for 2 minutes and then subjected to electrophoresis.

5. Determination of Dye to Protein Ratio

In order to prevent solubility problems with labeled proteins, conditions were chosen to only label 1–2% of the lysines in the cell extract. This is based on the assumption that 7% of an average protein's amino acids are lysine. The first step in determining the dye to protein ratio was the removal of free dye by adsorption to SM-2 beads (Bio-Rad). The protein concentration was determined by OD260/280. The dye content was determined by OD548 and OD650 for Propyl Cy-3 and Methyl Cy-5, respectively (=100,000 for both dyes).

EXAMPLE 3

Gel Electrophoresis

1. Two-dimensional Electrophoresis

High resolution two-dimensional gel electrophoresis was carried out by well known techniques.

2. SDS Polyacrylamide Gel Electrophoresis

SDS polyacrylamide gel electrophoresis was carried out by known techniques.

EXAMPLE 4

Fluorescence Gel Imaging

At the end of electrophoresis, the gels were soaked in a solution of 25% methanol and 7% acetic acid. The fluorescently labeled proteins in the gel were imaged in the following manner. Gels were placed on a surface of anodized aluminum and irradiated at an incident angle of 60° with a 300 W halogen lamp housed in a slide projector. The light exiting the projector was passed through 1' diameter bandpass filters (Chroma Technologies, Brattleboro Vt.), 545±10 nm and 635±15 nm for Cy-3 and Cy-5, respectively. The images were collected on a cooled, CCD camera (Photometrics Inc., Tucson Ariz.) fitted with a 50 mm lens (Nikon) and a double bandpass emission filter (Chroma Technologies, Brattleboro Vt.), 587.5±17.5 nm and 695±30 nm for Cy-3 and Cy-5, respectively. The CCD camera was controlled by a Macintosh II si computer running Photometrics camera controller software. Image integration time ranged from tenths of seconds to several minutes. The excitation filters were housed in a filter wheel attached to the projector. Two successive images were recorded with irradiation from the two filters without moving the gel.

EXAMPLE 5

Image Processing

The image files were transferred to a Personal Iris 4D/35 (Silicon Graphics Inc., Mountain View Calif.). The image files were then processed using the DeltaVision™ software (Applied Precision, Mercer Island Wash.). The two schemes were used to determine the differences between the differently labeled samples on the gel:

1. Subtraction

Each image can be considered as a grid-like array of pixel intensities. These arrays of values can be manipulated by a number of arithmetic operations. Here one image was subtracted from the other. Because the two samples loaded onto the gel were not perfectly balanced for overall fluorescence, one image was multiplied by a balancing constant. This factor was determined arbitrarily so that the number of differences between the samples were kept small.

2. Ratio Imaging

Here one image was divided by the other. Before this operation was performed the images were first normalized to a common intensity range. This was done by setting the minimum and maximum pixel values of each image to zero and an arbitrarily large value, 4095, the maximum possible output value of the CCD camera employed. Intermediate pixel values were scaled linearly between these values. One image was then divided by the other. A balancing factor was also used here to keep the mean quotient at one. Regions of difference were those with a quotient greater than one.

EXAMPLE 6

Figure 2:
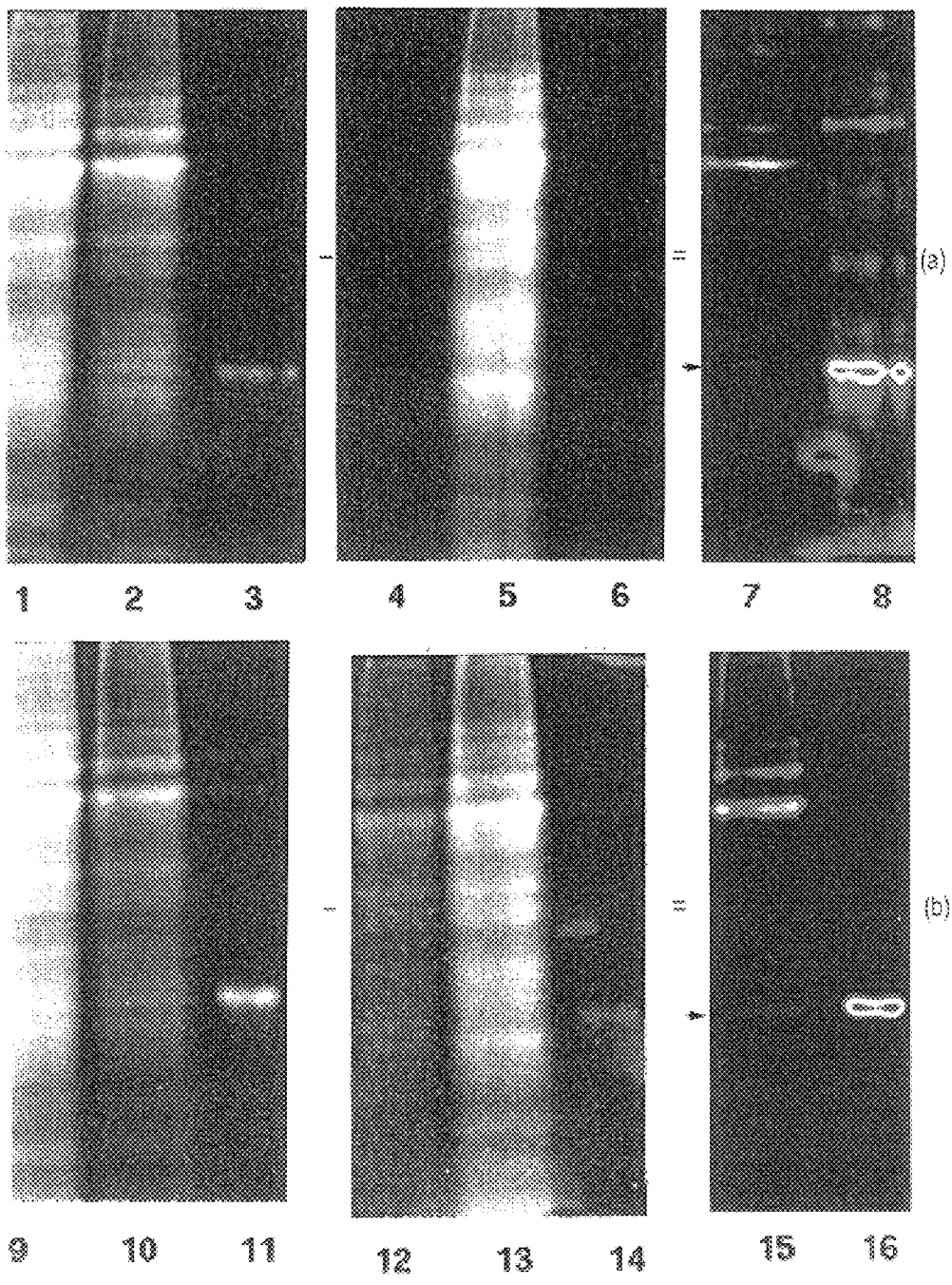
FIGS. 2a) and 2b) are images of proteins labeled with a preferred matched pair of labels of the present invention run on a single SDS polyacrylamide gel.

1. Difference SDS Gel Electrophoresis of Induced GAL4VP16 Expression in Bacteria FIG. 2 shows images of Propyl Cy-3 and Methyl Cy-5 labeled proteins run on a single SDS polyacrylamide gel. Lanes 1–3 show Cy-3 labeled protein. The samples loaded in there lanes were:

Lane 1. Propyl Cy-3 labeled IPTG-induced bacterial extract.

Lane 2. Propyl Cy-3 labeled IPTG-induced bacterial extract plus Methyl Cy-5 labeled uninduced extract.

Lane 3. Propyl Cy-3 labeled purified GAL4VP16 protein.

Lanes 4–6 show Cy-5 labeled protein. The samples loaded in there lanes were:

Lane 4. Propyl Cy-3 labeled IPTG-induced bacterial extract.

Lane 5. Propyl Cy-3 labeled IPTG-induced bacterial extract plus Methyl Cy-5 labeled uninduced extract.

Lane 6 Propyl Cy-3 labeled purified GAL4VP16 protein.

Only Lane 5 showed Cy-5 fluorescence.

Lanes 7 and 8 show the subtracted product of Lane 2–Lane 5 and Lane 3–Lane 6, respectively. The arrows point to the position of GAL4VP16 as confirmed by the position of the purified GAL4VP16 band in lane 8. The identity of the upper bands is not known. However, there are several proteins that are known to be induced by IPTG, including β-galactosidase.

Lanes 9–11 show Cy-5 labeled-protein. The samples loaded in these lanes were:.

Lane 9. Methyl Cy-5 labeled IPTG-induced bacterial extract.

Lane 10. Methyl Cy-5 labeled IPTG-induced bacterial extract plus Propyl Cy-3 labeled uninduced extract.

Lane 11. Methyl Cy-5 labeled purified GAL4VP16 protein.

Lanes 12–15 show Cy-5 labeled protein. The samples loaded in there lanes were:

Lane 12. Methyl Cy-5 labeled IPTG-induced bacterial extract.

Lane 13. Methyl Cy-5 labeled IPTG-induced bacterial extract plus Propyl Cy-3 labeled uninduced extract.

Lane 14. Methyl Cy-5 labeled purified GAL4VP16 protein.

Only Lanes 12–15 all showed some Cy-3 fluorescence. This is due to slight crossover between the bandpass filters. This causes Cy-5 labeled material to appear when excited by Cy-3 light. The converse is not seen. Cy-3 material is not visualized by Cy-5 excitation light. There are two ways to eliminate the crossover effects: design better bandpass filters or computationally remove the Cy-5 contribution to the Cy-3 image by knowing the crossover constant. Lanes 15 and 16 show the subtracted product of Lane 10–Lane 13 and Lane 11–Lane 14, respectively. The arrows point to the position of GAL4VP16 as confirmed by the position of the purified GAL4VP16 band in Lane 16. The identity of the upper bands is not known. However, there are several proteins that are known to be induced by IPTG, including β-galactosidase.

Figure 3:
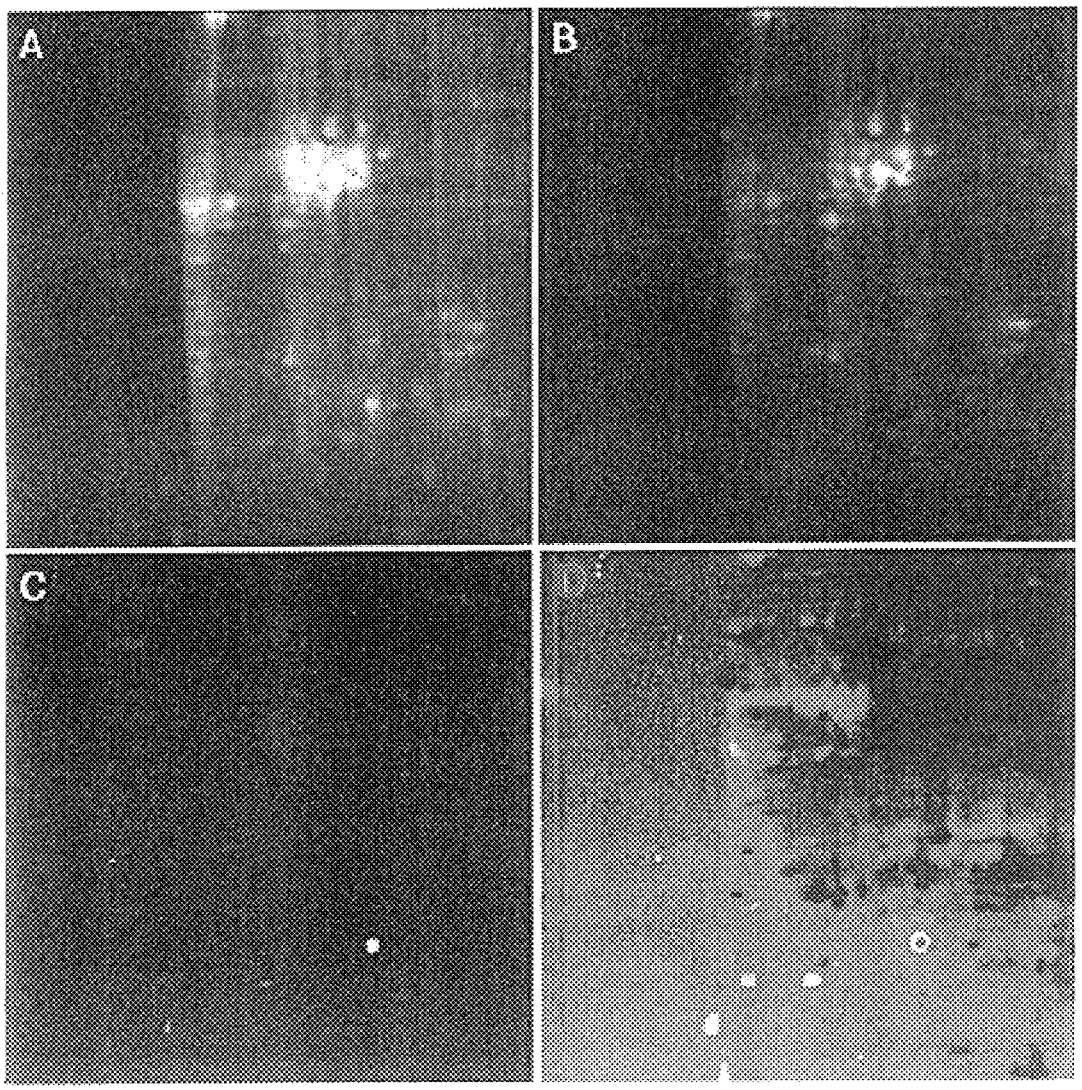
FIGS. 3a)–d) are images of portions of a two dimensional gel loaded with two different samples of bacterial extract, one IPTG-induced and the other uninduced, labeled with a different one of the dyes of the matched pair of dyes according to the process of the present invention.

2. Difference Two-dimensional Gel Electrophoresis of Induced GAL4VP16 expression in Bacteria FIG. 3 shows images of a portion, of a two-dimension gel loaded with Propyl Cy-3 labeled IPTG-induced bacterial extract plus Methyl Cy-5 labeled uninduced extract.

Panel A. Images taken with Cy-3 excitation light showing the IPTG-induced proteins.
Panel B. Images taken with Cy-5 excitation light showing the uninduced proteins.
Panel C. Ratio of the Cy-3 image divided by the Cy-5 image.
Panel D. Overlay of the image in Panel C, colored red, and placed on top of the image from Panel B, colored blue.

Figure 4:
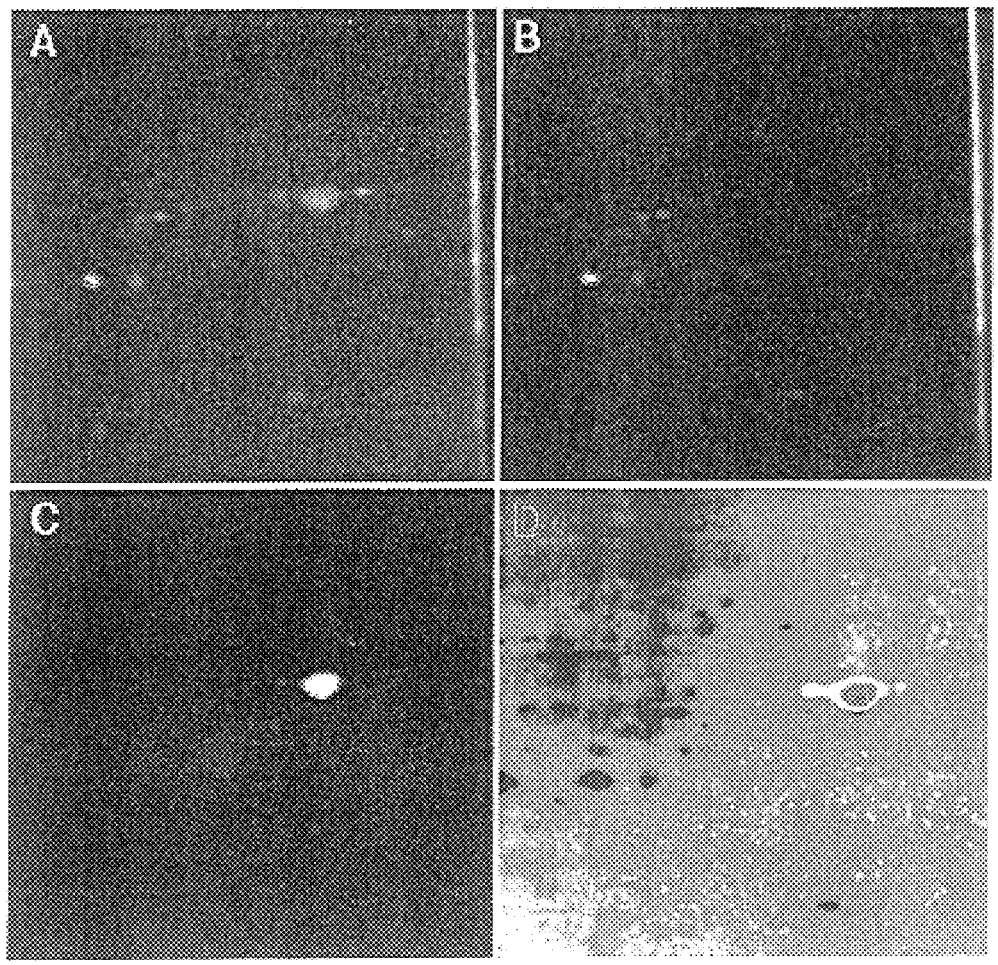
FIGS. 4a)–d) are images of portions of a two dimensional gel loaded with two different samples of bacterial extract, one having exogenously added carbonic anhydrase and one without carbonic anhydrase, each labeled with a different one of the dyes of the matched pair of dyes according to the process of the present invention.

3. Difference Two-dimensional Gel Electrophoresis of Bacteria Extract with Exogenously Added Protein FIG. 4 shows images of a portion of a two-dimension gel loaded with Propyl Cy-3 labeled bacterial extract that had exogenously added carbonic anhydrase plus Methyl Cy-5 labeled extract without the added carbonic anhydrase.

Panel A. Image taken with Cy-3 excitation light showing the bacterial proteins plus carbonic anhydrase.
Panel B. Images taken with Cy-5 excitation light showing the bacterial proteins alone.
Panel C. Ratio of the Cy-3 image divided by the Cy-5 image.
Panel D. Overlay of the image in Panel C, colored red, and placed on top of the image from Panel B, colored blue.

The process of the present invention provides a simple and inexpensive way to analyze the differences in protein content of different cells or different samples from other sources. The process eliminates problems which can occur using two separate gels which must be separately electrophoresed. The matched dyes used to label the different proteins allow simultaneous electrophoresis of two or more different samples in a single gel. While the invention has been described with reference to two samples of proteins and a matched pair of dyes, those skilled in the art will appreciate that more than two samples may be simultaneously tested using an equal number of matched dyes. As long as the spectral characteristics of the dyes can be manipulated to provide fluorescence at a number of different wavelengths resulting in visually distinct images and the pH and ionic characteristics of the dyes can be generally equalized to compensate for changes made to the protein by virtue of covalent bonding to the dye, multiple dyes can be used.

Differential Analysis of Glycoproteins

Dye Synthesis

EXAMPLE 7

Synthesis of the cyanine dye intermediates was as previously described. The carboxylic acid moiety of each of the Cy3 and Cy5 intermediates were then converted to hydrazide as detailed below.

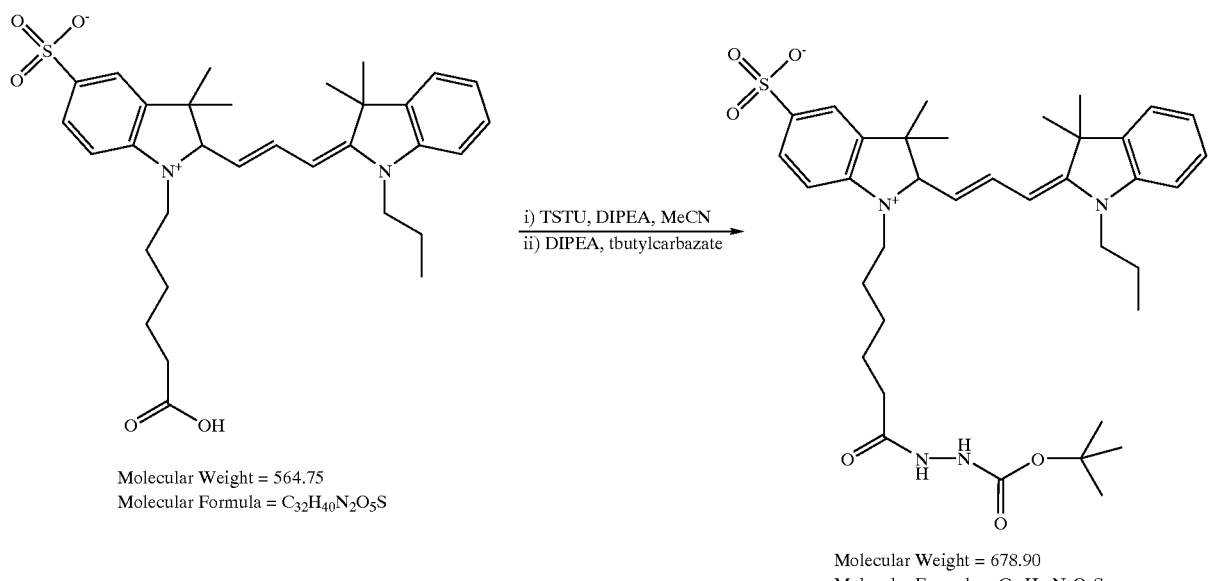

Molecular Weight = 564.75
Molecular Formula = $C_{32}H_{40}N_2O_5S$ i) TSTU, DIPEA, MeCN
ii) DIPEA, tbutylcarbazate Molecular Weight = 678.90
Molecular Formula = $C_{37}H_{50}N_4O_6S$ To a stirred solution of Cy-3 (50 mg, $8.9\times10^{-5}$ mol) dissolved in anhydrous acetonitrile (2 ml) under a nitrogen atmosphere was added diisopropylamine (0.03 ml, $9.7\times10^{-5}$ mol) and O—(N-succinimidyl)-N,N,N',N'-bis(tetramethyl) uronium tetrafluoroborate (TSTU) (30 mg, $9.7\times10^{-5}$ mol) and the reaction stirred at ambient temperature for 1 hour. Analysis of the material by thin layer chromatography (TLC) revealed that none of the starting material remained so an additional equivalent of diisopropylamine (0.03 ml, $9.7\times10^{-5}$ mol) was added which was then subsequently followed by tertbutyl carbazate (30 mg, $1.78\times10^{-4}$ mol). The reaction was stirred overnight at ambient temperature then the solvent removed in vacuo to give an intensely colored pink oil. The oil was purified using flash column chromatography (silica:dichloromethane/methanol gradient) resulting in a pink solid (59 mg, 97%). The product was clean and correct by $^1$H NMR and UV/VIS spectrometry ($\lambda_{max}$=552 nm).

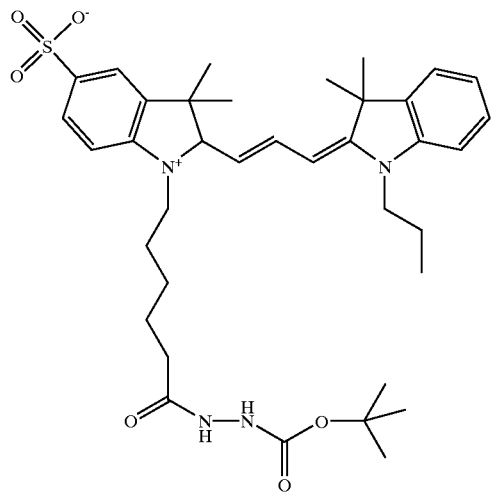

Molecular Weight = 678.90
Molecular Formula = C₃₇H₅₀N₄O₆S

TFA, CHCl₃ →

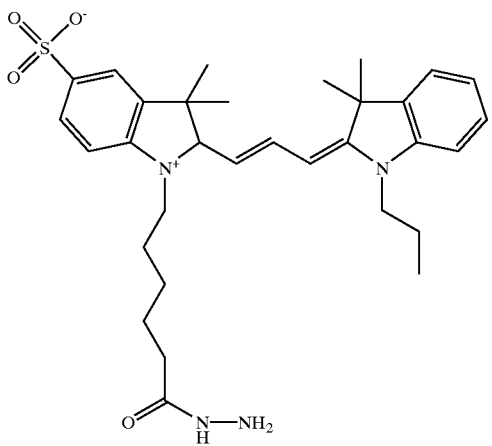

Molecular Weight = 578.78
Molecular Formula = C₃₂H₄₂N₄O₄S

Chloroform (1 ml) was added to a portion of the pink solid (5 mg) and a turbid solution resulted which was treated with trifluoroacetic acid (4 drops). After 1 hour incubation, TLC revealed that all the product had been consumed and a more polar product had been formed so the solvents were removed in vacuo and the resultant semi-solid was triturated with diethyl ether then dried in vacuo. The product appeared clean and correct by $^1$H NMR and UV/VIS spectrometry ($\lambda_{max}$=552 nm).

EXAMPLE 8

The preparation of Cy5 hydrazide is the same as that of Cy3 except that the starting material is Cy5.

EXAMPLE 9

Protein Labeling

1) Cell Culture

Initial experiments were performed on cultures of HBL 100 human breast, (see, In Vitro Cell & Dev. Biol., vol. 26, 933 (1990)), and BT474 human breast ductal carcinoma, (J. Natl. Cancer Inst. (Bethesda), vol. 61, 967 (1978)), epithelial cell lines. HBL100 cells were grown to confluence as a monolayer in McCoy's 5A media supplemented with 10% fetal bovine serum and 2 mM glutamine at 37° C. in 5% CO$_2$ in air atmosphere. BT474 cells were grown to confluence as a monolayer in RPMI 1460 media supplemented with 10% fetal bovine serum, 2 mM glutamine, 0.02 mg/ml bovine insulin, 0.45% glucose and 1 mM sodium pyruvate at 37° C. in 5% CO$_2$ in air atmosphere.

2) Protein Isolation from Cells

Flasks of cell monolayers were washed twice with PBS to remove media and the cells harvested by incubation in trypsin. The cell suspension was centrifuged at 2000 rpm for 5 minutes to pellet the cells. The supernatant was discarded and the cell pellet was washed with Tris to remove excess salt. The cell pellets were stored at −70° C. Protein was extracted from the cells by sonication. The cell pellets (~2×10$^6$ cells/ml) were resuspended in lysis buffer containing 2 M urea, 100 mM acetate buffer pH 5.5, 1% (v/v) NP-40 and 0.1% (w/v) SDS and sonicated on ice 4 times each for 20 seconds. The cell lysates were centrifuged at 4° C. at 13,000 rpm in a microfuge for 5 minutes to remove cell debris and the supernatant retained. Cell supernatants were stored at −20° C.

3) Protein Concentration Determination for Estimation of Dye:Protein Ratio

In order to prevent solubility problems with labeled proteins and to enable use of consistent dye:protein ratios, the concentration of extracted protein was determined by the BioRad Dc protein assay (BioRad Laboratories).

4) Labeling of Carbohydrate on Glycoproteins Using Hydrazide Dyes a) Labeling of model glycoproteins for SDS-PAGE i) Solutions of individual glycoproteins were prepared as 10 mg/ml stocks in water. 10 μg of each protein was taken for labeling and diluted with acetate buffer pH 5.5 to a final buffer concentration of 100 mM.

ii) Sugar residues were oxidized by addition of sodium metaperiodate in water to give a final concentration of 10 mM and incubated for 20 minutes at ambient temperature in the dark. Excess metaperiodate was removed by addition of sodium metabisulphite in 200 mM acetate buffer pH 5.5 to give a final concentration of 5 mM and incubated for 5 minutes at ambient temperature.

Cy3 hydrazide was added to the first cell sample and Cy5 hydrazide was added to the second cell extract at a concentration of ~25 nmol/10 μg protein. The dye stock solution was typically 10 mM in dimethylformamide. The labeling reaction was incubated at ambient temperature for 30 minutes. Incubation times may vary from about 10 to 60 minutes and the incubation temperature may vary from 0° C. to ~25° C. depending on the type of cells being studied. The temperature should not be above that which will cause the proteins to be degraded and the time should not be longer than that which could cause non-specific labeling.

iii) Gel loading sample buffer was added to labeled samples to give final concentrations of 2% (w/v) SDS, 10% (v/v) glycerol, 62.5 mM Tris-HCl pH 6.8, 5% (v/v) mercaptoethanol, 0.01% bromophenol blue. The sample was placed in a boiling water bath for 4 minutes then subjected to electrophoresis.

b) Labeling of simple glycoprotein mixtures for SDS-PAGE Simple mixtures of 12 or 14 different model proteins were prepared containing ~10 μg each of proteins from 10 mg/ml protein stock solutions to give a ladder of molecular weights. The protein solution was diluted 1:1 with 200 mM acetate buffer pH 5.5. The protein mixes were labeled according to the procedure described in step 4a (ii) above. Samples were analyzed by SDS-PAGE after addition of sample buffer as described.

c) Labeling of glycoproteins in cell extracts for 2-dimensional gel electrophoresis. Protein was extracted from cells as described in step 3 of this example and used directly for labeling of carbohydrate groups on glycoproteins. ~150 µg of extracted protein was labeled as described in step 4a (ii) above. Labeled samples (~25–50 µg) were mixed with 2×IEF sample buffer (8M urea, 4% (w/v) CHAPS, 2% (v/v) Pharmalytes, 20 mg/ml DTT) and loaded directly onto isoelectric focusing strips (Immobilized pH gradients, Amersham Pharmacia Biotech).

5) Labeling of Lysine Residues in Proteins Using NHS Dyes

Proteins were labeled on lysine residues with amine reactive NHS dyes as previously described using 200 pmol of Cy2-NHS ester/50 µg protein in 5 mM Tris buffer. Proteins from cell extracts were directly labeled with Cy2 as previously described.

6) Gel Electrophoresis

1. Two dimensional electrophoresis: high resolution two-dimensional electrophoresis was carried out by well known techniques according to Laemmli [Nature, vol. 227, 680–685 (1970)].

2. SDS-polyacrylamide gel electrophoresis: SDS-polyacrylamide gel electrophoresis was carried out by known techniques.

7) Fluorescence Gel Imaging

At the end of electrophoresis, the fluorescently labeled proteins in the gels were imaged using commercially available scanners with appropriate excitation and emission wavelengths [Cy2 excitation 480/30 emission 530/30; Cy3 excitation 540/25, emission 590/35; Cy5 excitation 620/30, emission 680/30].

EXAMPLE 10

Labeling of Model Glycoproteins

Figure 5:
FIGS. 5a) and b) are images of Cy2-NHS and Cy3 hydrazide labeled proteins run on SDS-PAGE, demonstrating that the hydrazide dyes specifically label the carbohydrate portion of the glycoprotein.
Figure 5:
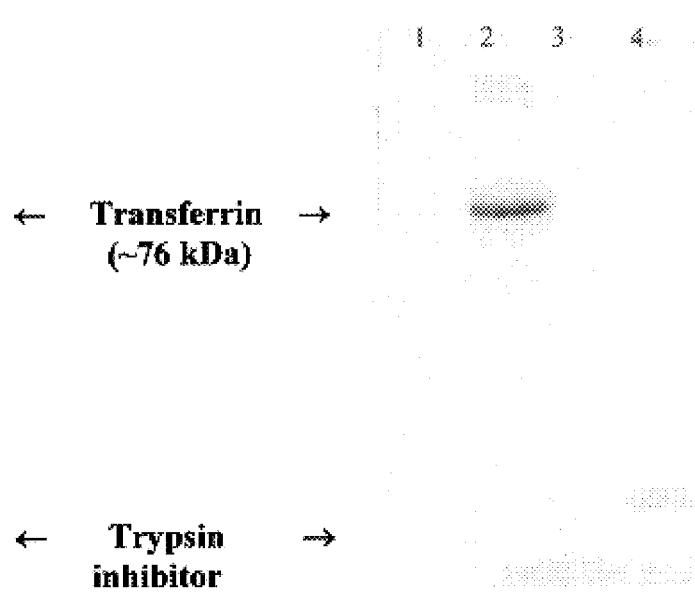

FIGS. 5a) and b), respectively, show images of Cy2-NHS and Cy3 hydrazide labeled proteins run on SDS-PAGE.

Lanes 1 and 3 show proteins labeled at lysine residues with Cy2 NHS ester visualized with Cy2 excitation and emission.

Lane 1. Cy2 labeled transferrin (molecular weight ~76 kDa).

Lane 3. Cy2 labeled soybean trypsin inhibitor (molecular weight ~20 kDa).

Lanes 2 and 4 show the same proteins labeled a carbohydrate groups with Cy3 hydrazide visualized with Cy3 excitation and emission.

Lane 2. Cy3 labeled transferrin.

Lane 4. Cy3 labeled soybean trypsin inhibitor.

Lanes 1 and 3 show that both transferrin and trypsin inhibitor are labeled with the Cy2 lysine dye. Lane 4 shows labeling of transferrin with Cy3 hydrazide. The trypsin inhibitor in lane 4 is not visible with Cy3 as this protein is not glycosylated and therefore does not label with Cy3.

EXAMPLE 11

Differential SDS-PAGE Analysis of Simple Protein Mixes

Figure 6:
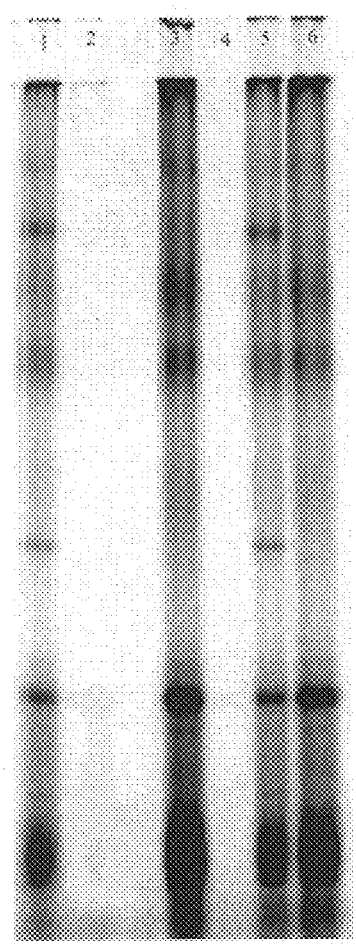
FIGS. 6a) and b) are images of Cy3 and Cy5 hydrazide labeled protein mixes on SDS-PAGE.
Figure 6:
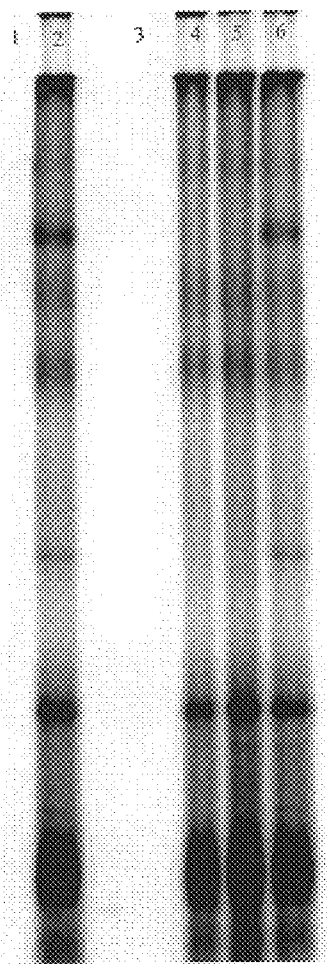

FIGS. 6a) and b) show images of Cy3 (6a) and Cy 5 (6b) hydrazide labeled protein mixes run on SDS-PAGE. Protein mix B was prepared by labeling 10 mg of each of the following proteins—fetuin, albumin, carboxypeptidase Y, ribonuclease B, α-1 acid glycoprotein, trypsin inhibitor, lactoglobulin, cytochrome C, α-lactalbumin, lysozyme, myoglobin and actin. Protein mix A contains identical proteins to mix B plus transferrin and carbonic anhydrase.

Lanes 1 and 3 of FIG. 6(a) show Cy3 labeled protein mixes A and B.

Lanes 2 and 4 of FIG. 6(b) show Cy5 labeled protein mixes A and B.

Lane 5 shows Cy3 labeled protein mix A plus Cy5 labeled protein mix B.

Lane 6 shows Cy5 labeled protein mix A plus Cy3 labeled mix B.

Lanes 5 and 6 with the protein mixes run in the same lane show differential detection of the two additional proteins in mix A—in lane 5 visible on the Cy3 image and in lane 6 visible on the Cy5 image.

EXAMPLE 12

Differential 2DE Analysis of Mammalian Cell Extracts

Figure 7:
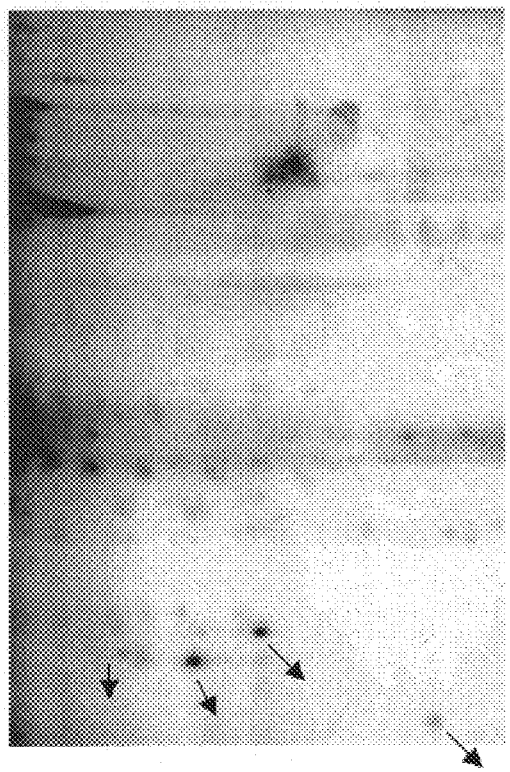
FIGS. 7a) and b) are images of a section of a 2DE gel loaded with Cy3 hydrazide labeled HBL100 cell extract and Cy5 hydrazide labeled BT474 cell extract.
Figure 7:
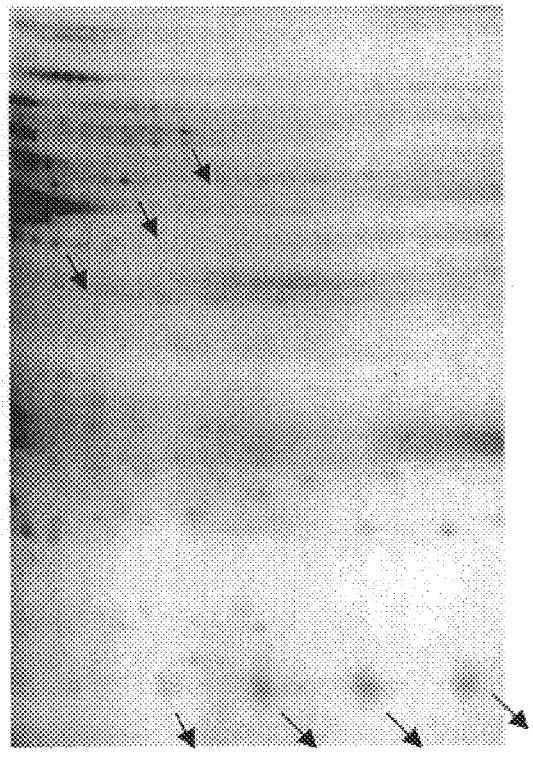

FIGS. 7(a) and (b) shows images of a section of a 2DE gel loaded with Cy3 (7a) hydrazide labeled HBL100 cell extract and Cy5 (7b) hydrazide labeled BT474 cell extract. Differences in the glycoprotein content of the cell lines are apparent from the different pattern of spots obtained with the two cell extracts. Some of the qualitative and quantitative differences have been highlighted with arrows.

EXAMPLE 13

Figure 8:
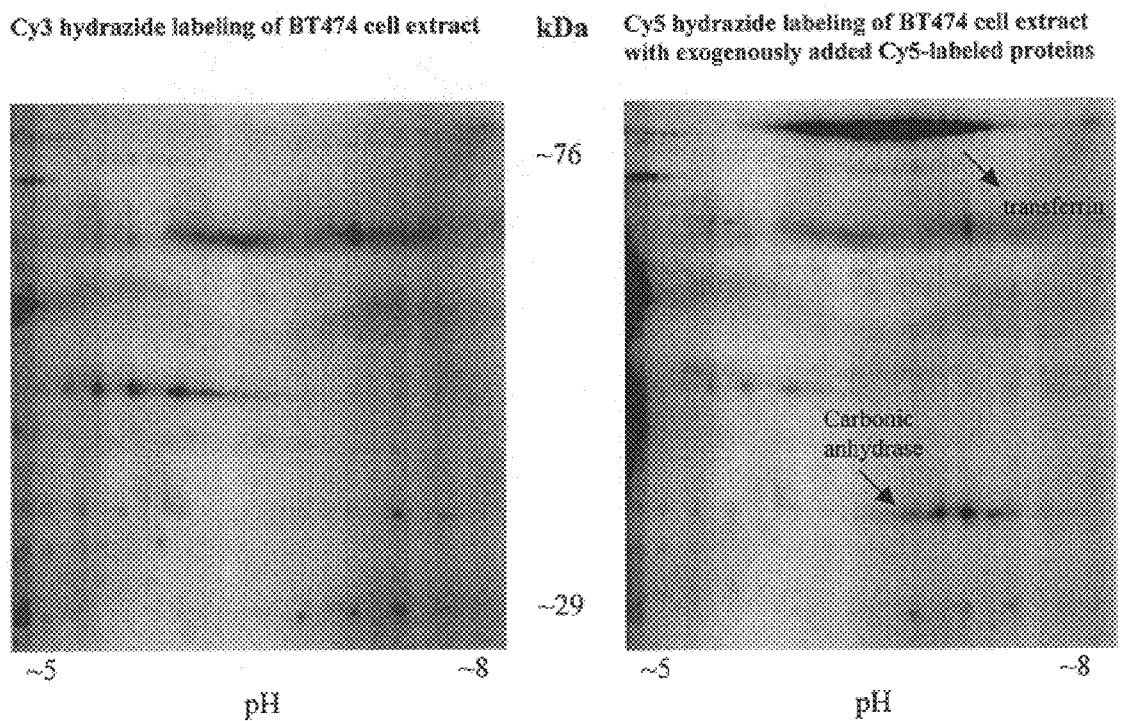
FIGS. 8a) and b) are images of a 2DE gel loaded with Cy3 hydrazide labeled BT474 cell extract without exogenously added protein and Cy5 hydrazide labeled BT474 cell extract with exogenously added protein.

Differential 2DE Analysis of Mammalian Cell Extract with Exogenously Added Protein Cell extracts were prepared as described in steps 1–4 of Example 9 above. To simulate differences in complex cell lysates the cell extracts were labeled with Cy3 and Cy5 hydrazide and Cy5 labeled known glycoproteins were added into Cy5 labeled sample. The Cy3 and Cy5 labeled samples were than mixed in equal volumes before 2DE. FIGS. 8a) and b) show images of a 2DE gel loaded with Cy3 (8a) labeled cell extract (without exogenously added protein) and Cy5 (8b) labeled cell extract with exogenously added protein. The added proteins were as follows:

| Protein | Molecular weight (kDa) | pI |
|---|---|---|
| transferrin | ~76 | ~6.3 |
| fetuin | ~70 | ~5 |
| carboxypeptidase-Y | ~58 | 6.3 (predicted)* |
| α-1 acid glycoprotein | ~45 | ~4.2 |
| albumin | ~45 | ~5.5 |
| carbonic anhydrase | ~30 | 7.9 (predicted) |

*From Prosite database

The section of gel highlighted shows proteins ranging in molecular weight from ~15–80 kDa and pH range 5–8. This portion thus excludes the proteins fetuin, α-1 acid glycoprotein and albumin from being detected in the Cy5 image.

The Cy3 and Cy5 images show good reproducibility in the spots detected using the two dyes to label the same BT474 cell sample and the differences can be attributed to the exogenously added proteins. Transferrin and carbonic anhydrase are highlighted on the Cy5 image but are not visible on the Cy3 image. The presence of carboxypeptidase-Y in the Cy5 sample has not been clearly demonstrated but this may be due to a number of causes such as overlap with endogenous cell proteins preventing it from being resolved or low level of carbohydrate on the protein.

Differential Protein Analysis by Column Chromatography

EXAMPLE 14

Protein Labeling

Proteins were labeled by means of a minimal labeling approach designed to add a single label onto each protein. This procedure results in only a small proportion of each protein being labeled. Protein levels indicated in the text below are total protein amount and do not take into account the proportion of protein actually labeled. Dyes containing a single net positive charge were reacted with primary amine groups on the protein to avoid change in overall charge status of the protein.

The N-hydroxysuccinimidyl esters of Cy3 and Cy5 derivatives matched for molecular weight (Amersham Pharmacia Biotech) containing a single positive charge were added to buffer (20 mM Tris/HCl pH7.6) containing protein or peptide at a ratio of 800 picomole dye per 200 microgram of protein in a total volume of 46 µl. The solution was incubated on ice in the dark for 30 minutes. The reaction was then stopped by the addition of 4 µl of 10 mM lysine solution and incubation on ice for a further 10 minutes.

Purified proteins were either labeled separately or mixed and then labeled. Anti-mouse immunoglobulin G (IgG) was obtained from the supplier (Amersham Pharmacia Biotech) ready labeled with either Cy3 or Cy5.

Instrumentation

An FPLC system (Amersham Pharmacia Biotech) consisting of pumps, valves and controller was used to pump samples through chromatography columns. The eluant from each column was fed into an 8 µl quartz flow-through cell (Hellma) positioned in an F4500 fluorimeter (Hitachi). The optics were not, however, optimized since the flowthrough cell had a vertical window and the light beam had a horizontal alignment, limiting the potential sensitivity of this particular system. Software designed to interrogate 2 excitation and emission wavelengths was used to allow continuous monitoring of the presence of Cy3 and Cy5 labeled proteins. For detection of Cy3, wavelength settings used were 530 nm (excitation) and 570 nm (emission). For detection of Cy5, settings were 630 nm (excitation) and 670 nm (emission). Slit widths for excitation and emission were 10 nm.

Chromatography

Cy3 and Cy5 labeled proteins or peptides were detected simultaneously and continuously on elution from chromatography columns. Mixtures of proteins or peptides were profiled on a variety of column types. Differences between two protein samples could also be examined by labeling the samples with different fluors and then mixing followed by chromatography and simultaneous detection of the fluorescence of the two fluors.

EXAMPLE 15

Ion Exchange Column

MonoQ HR5/5 anion exchange column (50×5 mm internal diameter) (Amersham Pharmacia Biotech) was equilibrated with starting buffer (20 mM Tris/HCl pH 7.6). Protein samples made up in starting buffer were applied to the column using a 100 µl loop. Proteins were eluted from the column using a linear gradient of the same buffer containing 350 mM NaCl over a 25 minute period at a flow rate of 0.5 ml per minute. Cy3 and Cy5 labeled proteins were detected simultaneously and continuously on elution from the ion exchange column.

Figure 9:
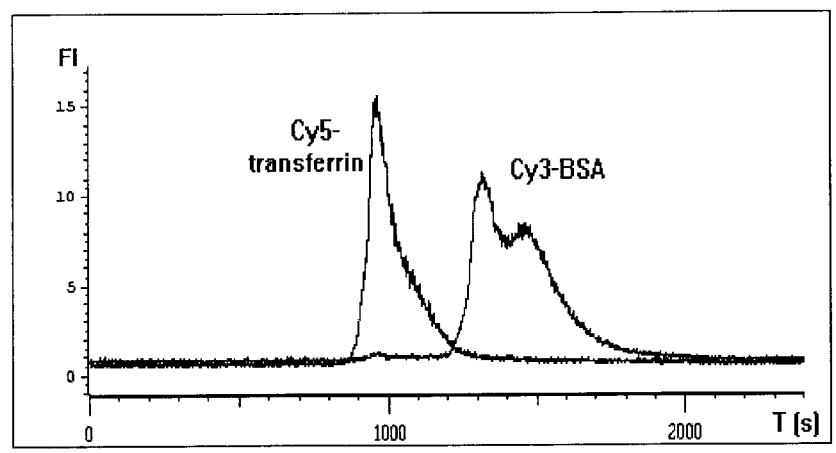
FIG. 9 is a graph showing the results of ion exchange chromatography of Cy3 labeled bovine serum albumin (BSA;33 $\mu$g) and Cy5 labeled transferrin (33 $\mu$g).

FIG. 9 shows the separation of Cy3 labeled bovine serum albumin (BSA) and Cy5 labelled transferrin.

Figure 10:
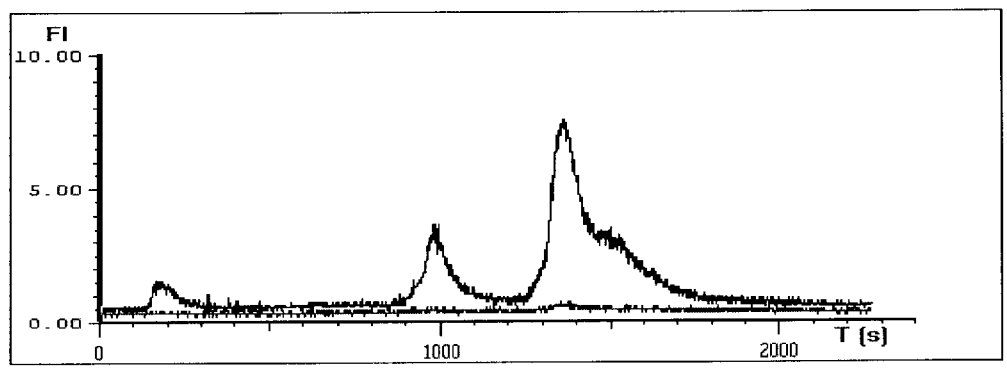
FIG. 10 is a graph showing the results of ion exchange chromatography of Cy5 labeled myglobin, transferrin and bovine serum albumin (13 $\mu$g of each protein).

FIG. 10 shows the separation of the mixture of Cy5 labeled myoglobin, transferrin and bovine serum albumin.

Figure 14:
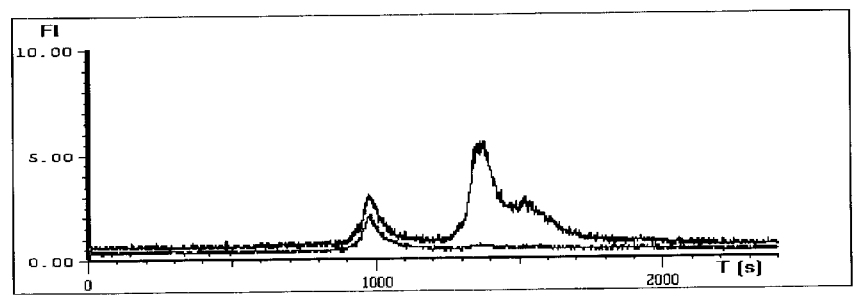
FIG. 14 is a graph showing the results of differential analysis by ion exchange chromatography, of Cy3 or Cy5 labeled samples. Cy3 labeled sample contained transferrin and Cy5 labeled sample contained transferrin and bovine serum albumin (13 µg of each protein). Cy3 and Cy5 labeled samples were mixed prior to chromatography.

Differential analysis by ion exchange chromatography and fluorescence detection is shown in FIG. 14. One sample containing Cy3 labeled transferrin has been mixed with another sample containing Cy5 labeled transferrin and Cy5 labeled bovine serum albumin (BSA). The absence of BSA from the second sample is clear.

EXAMPLE 16

Reverse Phase Column

A ProRPC column (silica based C1/C8 mix)(100×5 mm internal diameter) was equilibrated with a mix of eluant A (70%) and eluant B (30%). Eluant A contained 0.1% trifluoroacetic acid, 0.1% triethylamine in water (95%) acetonitrile (5%). Eluant B contained 0.1% trifluoroacetic acid, 0.1% triethylamine in water (25%) acetonitrile (75%). Protein samples made up in eluant A were applied to the column using a 100 µl loop and eluted using a linear gradient from 70% eluant A/30% eluant B to 20% eluant A/80% eluant B over a 25 minute period at a flow rate of 0.5 ml per minute. Cy3 and Cy5 labeled proteins were detected simultaneously and continuously on elution from the reverse phase column.

Figure 11:
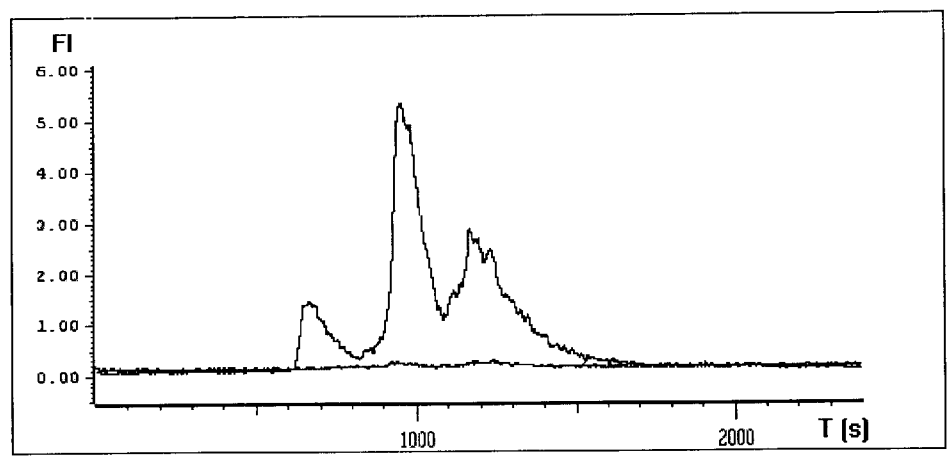
FIG. 11 is a graph showing the results of reverse phase chromatography of Cy5 labeled ribonuclease a, cytochrome c, holo-transferrin and apomyoglobin (3.3 $\mu$g of each protein).

FIG. 11 shows the reverse phase separation of the mixture of Cy5 labeled ribonuclease A, cytochrome C, holotransferrin and apomyoglobin.

EXAMPLE 17

Size Exclusion Column

A Superose 6 HR10/30 column (300×10 mm internal diameter) (Amersham Pharmacia Biotech) was equilibrated with 10 mM phosphate buffered saline (PBS) pH 7.4. Protein samples made up in the same buffer were applied to the column using a 100 µl loop and eluted at a flow rate of 0.5 ml per minute. Cy3 and Cy5 labeled proteins were detected simultaneously and continuously on elution from the size exclusion column.

Figure 12:
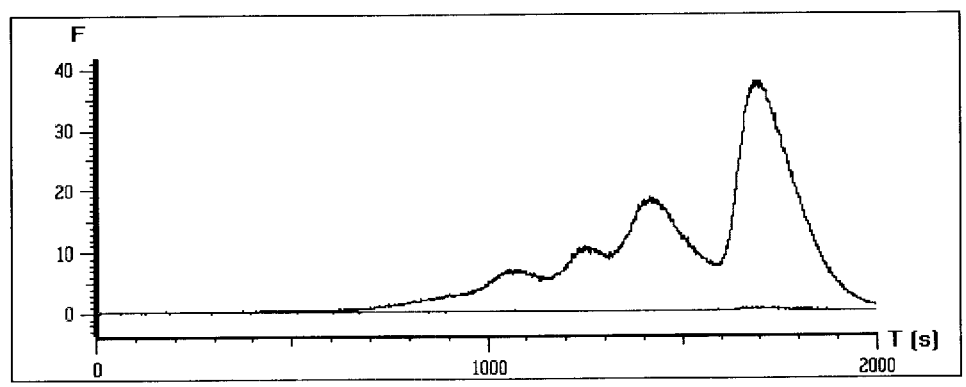
FIG. 12 is a graph showing the results of size exclusion chromatography of Cy3 labeled thryoglobulin, apoferritin, IgG and β-lactoglobulin (23.5 $\mu$g of each protein).

FIG. 12 shows the separation of the mixture of Cy3 labeled thyroglobulin, apoferritin, IgG and β-lactoglobulin by size exclusion chromatography.

Figure 13:
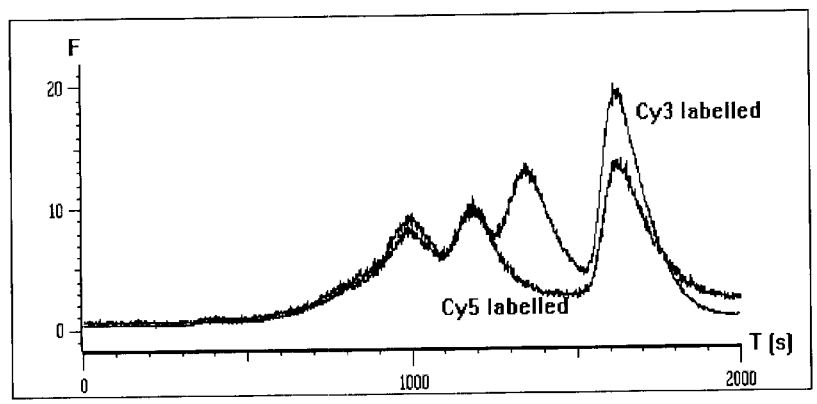
FIG. 13 is a graph showing the results of differential protein analysis by size exclusion chromatography using samples labeled with Cy3 or Cy5. The Cy3 labeled protein are thryoglobulin (38 $\mu$g), apoferritin (28 $\mu$g), IgG (2.6 $\mu$g),and β-lactoglobulin (12 $\mu$g). The Cy 5 labeled sample does not contain IgG. Cy3 and Cy5 labeled samples were mixed prior to chromatography.

FIG. 13 shows differential analysis by size exclusion chromatography. The Cy3 labeled sample contains four proteins (thryoglobulin, apoferritin, IgG and β-lactoglobulin) and the Cy5 labeled sample shows just three of the four proteins (minus IgG). The absence of the fourth protein is clear.

EXAMPLE 18

Differential Protein Analysis by Affinity Purification

Cell Growth, Lysis and Affinity Purification

Lysates of *E coli* bacteria either expressing GST or not expressing GST were used as models of complex protein samples. *E coli* strain JM109 cells were transformed either with plasmid pGEX-5X which encodes GST or with control plasmid pTrc99 which does not encode GST (plasmids from Amersham Pharmacia Biotech) and plated out onto agar plates. Liquid cultures (10 ml) were then grown overnight at 37° C. in LB broth containing 100 µg/ml ampicillin. Fresh media (typically 150 ml) was then inoculated with 0.5% starting culture and grown to an $A_{600}$ of 1.0. The cells were then induced by addition of IPTG to a final concentration of 0.5 mM and incubating for a further 2 to 3 hours. Cells were harvested by centrifugation at 2800 g, taken up in 7.5 ml PBS and lysed by sonication (MSE 150 Soniprep) on ice (30 seconds, rest for 90 seconds, repeated 3 times). Cell debris was removed by centrifugation at 2800 g and after transfer of the supernatant to a fresh tube the centrifugation was repeated. The supernatant (100 µl aliquot normalized with respect to concentration determined by $A_{280}$ reading) was then labeled with 1.5 nmol Cy dye on ice in the dark for 60 minutes and quenched with lysine as above.

At this point, the lysates were either treated separately or they were mixed, for example a sample of pGEX cell lysate labeled with Cy3 being mixed with an equal volume of pTrc cell lysate labeled with Cy5. GST was then affinity purified from the cell extract using Glutathione Sepharose 4B (cat. no. 17-0756-01, Amersham Pharmacia Biotech) using the batch method protocol provided by the supplier for fusion protein screening.

Samples were read in the Hitachi fluorimeter exciting Cy3 at 530 nm (emission peak detected at 565 nm) and exciting Cy5 at 630 nm (emission peak detected at 661 nm) using 5 nm slits for excitation and emission. Material which did not bind to the affinity matrix was combined with washings for fluorescence determination. Material bound to the affinity matrix was eluted using excess unlabeled GST. Prior to reading, a 15 µl aliquot of each sample was diluted into a total volume of 100 µl. Wash trough samples were diluted a further 10 fold prior to reading because of their relatively high values. Subsequently, readings were corrected to take into account the relative volumes and dilutions of bound and wash through fractions.

Affinity Purification

Differential analysis by affinity purification was used to identify a specific protein (glutathione-S-transferase, GST) in a cell lysate. Initial experiments demonstrated that in bacterial cell lysates labeled with either Cy 3 or Cy 5 and analysed separately, the presence of GST could be determined. Samples from induced bacteria containing the pGEX plasmid which encodes for GST clearly contained GST protein as indicated by fluorescent material specifically eluted from the affinity glutathione matrix with free glutathione (Table 1). This material was confirmed to be GST by imaging the fluorescence of an SDS-PAGE gel containing Cy5-labeled purified CST (Sigma) and affinity purified GST as described above. Samples from induced bacteria containing the pTrc plasmid which does not encode for GST but is otherwise very similar, did not appear to contain GST protein. This conclusion is indicated by a low level of fluorescent material eluted from the affinity matrix and the absence of a fluorescent band of correct molecular weight on an SDS-PAGE gel.

TABLE 1

Affinity purification of GST from cell lysates labeled either with Cy3 or Cy5, lysates processed separately for affinity purification.

| Sample | Experiment 1 Relative Cy3 fluorescence ($F_{565}$)* | Experiment 2 Relative Cy5 fluorescence ($F_{661}$)* |
|---|---|---|
| pGEX cell lysate fraction bound to affinity matrix | 62.1 | 99.8 |
| pTrc cell lysate fraction bound to affinity matrix | 2.6 | 5.3 |
| pGEX cell lysate washed through affinity matrix | 13118 | 13487 |
| pTrc cell lysate washed through affinity matrix | 13232 | 16320 |

*Readings corrected for differences in dilution and volume.

Subsequent experiments showed that when two separate lysates were labeled with different dyes and mixed prior to affinity purification, differences in the GST content of the two samples could be determined by means of their relative fluorescence. For example, Cy3-labeled induced pGEX cell lysate was mixed with Cy5-labeled induced pTrc cell lysate and affinity purified. The proportion of material bound contained in the GST expressing cells was more than 10 times higher than that in cells not expressing GST (Table 2). In the next sample, Cy3-labeled induced pGEX cell lysate was mixed with Cy5-labeled non-induced pGEX cell lysate and affinity purified. The proportion of material bound contained in the GST expressing cells was again more than 10 times higher than that in cells not expressing GST (Table 2).

TABLE 2

Affinity purification of GST from cell lysates labeled either with Cy3 or Cy5, lysates mixed prior to affinity purification.

| Sample | Proportion bound (%) | Proportion bound (%) |
|---|---|---|
| Material from Cy3-labeled induced pGEX cell lysate mixed with Cy5-labeled induced pTrc cell lysate bound to affinity matrix | 3.3 | 0.28 |
| Material from Cy3-labeled induced pGEX cell lysate mixed with Cy5-labeled non-induced pGEX cell lysate bound to affinity matrix | 3.8 | 0.32 |

What we claim is:

1. A method of comparing protein compositions between at least two different cell samples comprising:

(a) preparing an extract of proteins from each of said at least two cell samples;

(b) providing a set of matched luminescent dyes chosen from dyes capable of covalently binding to proteins within said extract of proteins, wherein each dye within said set
  (1) has a net charge which will maintain the overall net charge of the proteins upon such covalent binding and has ionic and pH characteristics whereby relative migration of a protein labeled with any one of said dyes is the same as relative migration of said protein labeled with another dye in said set,
  (2) emits luminescent light at a wavelength that is sufficiently different from the emitted luminescent light of remaining dyes in said set to provide a detectably different light signal;

(c) reacting each extract of proteins of step (a) with a different dye from said set of step (b) to provide dye-labeled proteins;

(d) mixing each of said dye labeled proteins to form a single mixture of different dye-labeled proteins;

(e) separating the dye-labeled proteins of interest within said mixture; and (f) detecting the difference in luminescent intensity between the different dye-labeled proteins of interest by luminescent detection.

2. The method of claim 1 wherein said dyes bind to a primary amine of a lysine residue of the protein and each said dye within said luminescent dyes carries a net +1 charge.

3. The method of claim 1 wherein said set of matched luminescent dyes are cyanine dyes having the following structure:

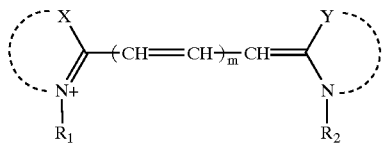

wherein the dotted lines each represent carbon atoms necessary for the formation of one to three fused rings having five to six atoms in each ring, X and Y are selected from the group consisting of S, O and $CH_3$—C—$CH_3$, m is an integer from 1 to 3, one of $R_1$ and $R_2$ is a reactive group and the other is an alkyl.

4. The method of claim 1 wherein each dye has at least one reactive group selected from the group consisting of isothiocyanate, isocyanate, N-hydroxysuccinimidyl ester, imido ester, glyoxal, carboxylic acid, haloacetamide, maleimide, alkyl halide, acid halide, azide, hydrazide, hydrazine, ketone and amino.

5. The method of claim 1 wherein said set of matched luminescent dyes are neutral dyes bound to the primary amino of a lysine residue in the protein by a positively charged linker group.

6. The method of claim 1 wherein said set of matched luminescent dyes are neutral dyes bound to a sulfhydryl group in the protein.

7. The method of claim 1 wherein said set of matched luminescent dyes are derivatives of dipyrromethene boron difluoride dyes.

8. The method of claim 1 wherein separating the dye-labeled proteins is by an electrophoretic method.

9. The method of claim 8 wherein the electrophoretic method comprises one dimensional gel electrophoresis, two dimensional gel electrophoresis, capillary zone electrophoresis, capillary gel electrophoresis, capillary isoelectric focusing, isotacophoresis, or micellar electrokinetic chromatography.

10. The method of claim 1 wherein separating the dye-labeled proteins is by a chromatographic method.

11. The method of claim 10 wherein the chromatographic method comprises affinity chromatography, size exclusion chromatography, reverse phase chromatography, hydrophobic interaction chromatography or ion exchange chromatography.

12. The method of claim 1 further comprising quenching the reaction between the proteins and the dyes prior to mixing said dye labeled proteins.

13. The method of claim 1 wherein the step of detecting differences in emitted color is by fluorescent microscopy.

14. The method of claim 1 wherein the step of detecting differences in emitted color is by electronic imaging.

15. The method of claim 1 wherein the proteins have binding sites for covalent binding to said dyes selected from the group consisting of lysine, carboxylic acid and sulfhydryl groups.

16. The method of claim 1 wherein the proteins include glycoproteins having terminal sugar groups and preparing the extract of proteins further comprises the step of oxidizing terminal sugar groups to form aldehyde groups; and each dye of said set has a reactive group capable of forming a covalent bond with the aldehyde group.

17. The method of claim 1 wherein the proteins include phosphoproteins.

18. The method of claim 1 wherein preparing the extract of proteins further comprises digesting at least a portion of the proteins with enzyme for generating peptides.

19. A method of comparing proteins of interest between at least two different samples comprising:

(a) preparing a mixture of proteins from each of said at least two samples;
(b) providing a set of matched luminescent dyes chosen from dyes capable of covalently binding to said proteins within said mixture of proteins, wherein each dye within said set
  (1) has ionic and pH characteristics whereby relative migration of a protein labeled with any one of said dyes is the same as relative migration of said protein labeled with another dye in said set,
  (2) emits luminescent light at a wavelength that is sufficiently different from the emitted luminescent light of remaining dyes in said set to provide a detectably different light signal;
(c) reacting each said mixture of proteins of step (a) with a different dye from said set of step (b) to provide dye-labeled proteins;
(d) mixing each of said dye labeled proteins to form a combined single mixture of different dye-labeled proteins;
(e) separating the different dye-labeled proteins of interest within said combined mixture; and
(f) detecting the difference in luminescent intensity between the different dye-labeled proteins of interest by luminescent detection.

20. The method of claim 19 wherein said set of matched luminescent dyes are cyanine dyes having the following structure:

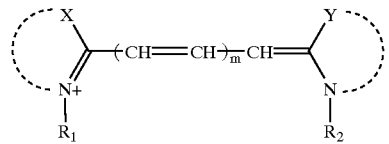

wherein the dotted lines each represent carbon atoms necessary for the formation of one to three fused rings having five to six atoms in each ring, X and Y are each selected from the group consisting of O, S and $CH_3$—C—$CH_3$, m is an integer from 1 to 3, one of $R_1$ and $R_2$ is a reactive group and the other is an alkyl.

21. The method of claim 19 wherein each dye has at least one reactive group selected from the group consisting of isothiocyanate, isocyanate, N-hydroxysuccinimidyl ester, imido ester, glyoxal, carboxylic acid, haloacetamide, maleimide, alkyl halide, acid halide, azide, hydrazide, hydrazine, ketone and amino.

22. The method of claim 19 wherein the proteins have binding sites selected from the group consisting of lysine, carboxylic acid and sulfhydryl groups.

23. The method of claim 19 wherein separating the dye-labeled proteins is by an electrophoretic method.

24. The method of claim 23 wherein the electrophoretic method comprises one dimensional gel electrophoresis, two dimensional gel electrophoresis, capillary zone electrophoresis, capillary gel electrophoresis, capillary isoelectric focusing, isotacophoresis, or micellar electrokinetic chromatography.

25. The method of claim 19 wherein separating the dye-labeled proteins is by a chromatographic method.

26. The method of claim 25 wherein the chromatographic method comprises affinity chromatography, size exclusion chromatography, reverse phase chromatography, hydrophobic interaction chromatography or ion exchange chromatography.

27. The method of claim 19 wherein the proteins are glycoproteins having terminal sugar groups and preparing the extract of proteins further comprises the step of oxidizing terminal sugar groups to form aldehyde groups; and each dye of said set has a reactive group capable of forming a covalent bond with the aldehyde group.

28. The method of claim 19 wherein the proteins are phosphoproteins and the dye includes an imidazole group, said method further comprising adding carbodiimide to said mixture of proteins and dyes for the reaction of step (c).

29. The method of claim 19 wherein preparing the extract of proteins further comprises digesting at least a portion of the proteins with enzyme for generating peptides.

30. A method of comparing proteins of interest between at least two different samples comprising:
  (a) preparing a mixture of proteins from each of said at least two samples;
  (b) providing a set of matched luminescent dyes chosen from a single class of dyes capable of covalently binding to proteins within said mixture of proteins, wherein each dye within said set
    (1) has ionic and pH characteristics whereby relative migration of a protein labeled with any one of said dyes is the same as relative migration of said protein labeled with another dye in said set,
    (2) emits luminescent light at a wavelength that is sufficiently different from the emitted luminescent light of remaining dyes in said set to provide a detectably different light signal;
  (c) reacting each mixture of proteins of step (a) with a different dye from said set of step (b) to provide dye-labeled proteins;
  (d) mixing each of said dye labeled proteins to form a combined single mixture of different dye-labeled proteins;
  (e) separating different dye-labeled proteins of interest within said combined mixture; and
  (f) detecting the difference in luminescent intensity between the different dye-labeled proteins of interest by luminescent detection.

31. The method of claim 30 wherein separating the dye-labeled proteins is by an electrophoretic method.

32. The method of claim 31 wherein the electrophoretic method comprises one dimensional gel electrophoresis, two dimensional gel electrophoresis, capillary zone electrophoresis, capillary gel electrophoresis, capillary isoelectric focusing, isotacophoresis, or micellar electrokinetic chromatography.

33. The method of claim 30 wherein separating the dye-labeled proteins is by a chromatographic method.

34. The method of claim 33 wherein the chromatographic method comprises affinity chromatography, size exclusion chromatography, reverse phase chromatography, hydrophobic interaction chromatography or ion exchange chromatography.

35. The method of claim 30 wherein the proteins are glycoproteins having terminal sugar groups and preparing the extract of proteins further comprises the step of oxidizing terminal sugar groups to form aldehyde groups; and each dye of said set has a reactive group capable of forming a covalent bond with the aldehyde group.

36. The method of claim 30 wherein preparing the extract of proteins further comprises digesting the proteins with enzyme for generating peptides.

37. The method of claim 30 wherein the proteins are phosphoproteins and the dye includes an imidazole group, said method further comprising adding carbodiimide to said mixture of proteins and dyes for the reaction of step (c).

38. The method of claim 30 wherein each dye has at least one reactive group selected from the group consisting of isothiocyanate, isocyanate, N-hydroxysuccinimidyl ester, imido ester, glyoxal, carboxylic acid, haloacetamide, maleimide, alkyl halide, acid halide, azide, hydrazide, hydrazine, ketone and amino.

39. A method of comparing protein compositions between at least two different cell samples comprising:
  (a) preparing an extract of proteins from each of said at least two cell samples;
  (b) providing a set of matched luminescent dyes chosen from dyes capable of covalently binding to proteins within said extract of proteins, wherein each dye within said set
    (1) has a net charge which will maintain the overall net charge of the proteins upon such covalent binding and has ionic and pH characteristics whereby relative migration of a protein labeled with any one of said dyes is the same as relative migration of said protein labeled with another dye in said set, and,
    (2) emits luminescent light at a wavelength that is sufficiently different from the emitted luminescent light of remaining dyes in said set to provide a detectably different light signal;
  (c) reacting each extract of proteins of step (a) with a different dye from said set of step (b) to provide dye-labeled proteins;
  (d) mixing said dye labeled proteins to form a single mixture of different dye-labeled proteins;
  (e) separating the dye-labeled proteins within said mixture by a chromatographic method; and
  (f) detecting the difference in luminescent intensity between the different dye-labeled proteins of interest by luminescent detection.

* * * * *